US009428518B2

(12) United States Patent
Wonneberger et al.

(10) Patent No.: US 9,428,518 B2
(45) Date of Patent: Aug. 30, 2016

(54) PERYLENEMONOIMIDE AND NAPHTHALENEMONOIMIDE DERIVATIVES AND THEIR USE IN DYE-SENSITIZED SOLAR CELLS

(71) Applicants: BASF SE, Ludwigshafen (DE); Max-Planck-Gesellschaft zur Foerderung der Wissenschaften e.V., Munich (DE)

(72) Inventors: Henrike Wonneberger, Mannheim (DE); Neil Gregory Pschirer, Ludwigshafen (DE); Flavio Luiz Benedito, Ludwigshafen (DE); Ingmar Bruder, Mutterstadt (DE); Robert Send, Karlsruhe (DE); Yulian Zagranyarski, Sofia (BG); Chen Li, Cologne (DE); Klaus Muellen, Cologne (DE); Long Chen, Mainz (DE); Artem Nikolaevich Skabeev, Mainz (DE)

(73) Assignees: BASF SE, Ludwigshafen (DE); Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 0 days.

(21) Appl. No.: 14/772,488

(22) PCT Filed: Mar. 12, 2014

(86) PCT No.: PCT/IB2014/059678
§ 371 (c)(1),
(2) Date: Sep. 3, 2015

(87) PCT Pub. No.: WO2014/147525
PCT Pub. Date: Sep. 25, 2014

(65) Prior Publication Data
US 2016/0024106 A1    Jan. 28, 2016

Related U.S. Application Data

(60) Provisional application No. 61/802,812, filed on Mar. 18, 2013.

(30) Foreign Application Priority Data

Mar. 18, 2013 (EP) ..................... 13159804

(51) Int. Cl.
*C07D 471/08* (2006.01)
*C07D 493/08* (2006.01)
(Continued)

(52) U.S. Cl.
CPC ........... *C07D 491/06* (2013.01); *C07D 221/04* (2013.01); *C07D 471/06* (2013.01);
(Continued)

(58) Field of Classification Search
USPC ................ 546/31, 49; 549/25, 232; 136/252
See application file for complete search history.

(56) References Cited

U.S. PATENT DOCUMENTS 3,989,520 A * 11/1976 Rochlitz ................ G03G 5/047
430/128
4,927,721 A    5/1990 Graetzel et al.
(Continued)

FOREIGN PATENT DOCUMENTS

DE       1794381    *  1/1974 ............ C09B 57/00
EP    1 172 418 A2     1/2002
(Continued)

OTHER PUBLICATIONS

International Search Report Jan. 12, 2015 in corresponding PCT/IB2014/059678 filed Mar. 12, 2014.
(Continued)

*Primary Examiner* — Charanjit Aulakh
(74) *Attorney, Agent, or Firm* — Oblon, McClelland, Maier & Neustadt, L.L.P

(57) ABSTRACT

A sensitizer in a dye-sensitized solar cell, including a compound of formula (I')

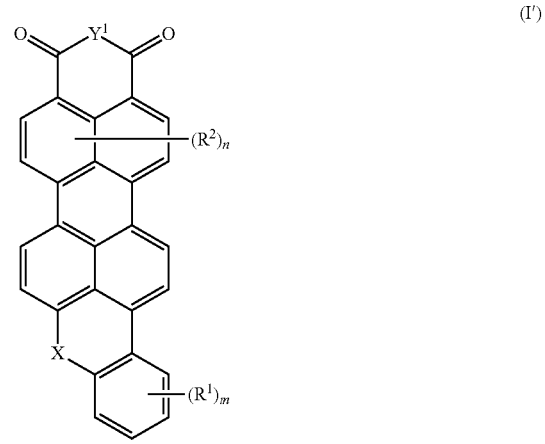

where: $R^1$ and $R^2$ are hydrogen, a halogen, an alkyl group, a cycloalkyl group, an aryl group, a hetaryl group, an alkoxy group, an aryloxy group, an arylthio group, a hetaryloxy group, a hetarylthio group, a diarylamino group, or a dialkylamino group; m, n are each independently an integer from 0-4; X is sulfur, oxygen, or $NR^3$, where $R^3$ is hydrogen, an alkyl group, a cycloalkyl group, an aryl group, or a hetaryl group; $Y^1$ is oxygen or N—Z-A, where A is —COOM, —$SO_3M$, or —$PO_3M$, where M is hydrogen, an alkali metal cation, or $[NR']^{4+}$, where each R' is independently hydrogen or an alkyl group, and where Z is $C_1$-$C_6$-alkylene or 1,4-phenylene, where the phenylene radical is optionally substituted by one or more alkyl, nitro, cyano, and halogen substituents.

6 Claims, 6 Drawing Sheets

(51) Int. Cl.
- H01L 51/42 (2006.01)
- C07D 491/06 (2006.01)
- H01L 51/00 (2006.01)
- C07D 221/04 (2006.01)
- C07D 471/06 (2006.01)
- C07D 493/06 (2006.01)
- C07D 495/06 (2006.01)
- C09B 5/62 (2006.01)
- H01G 9/20 (2006.01)

(52) U.S. Cl.
CPC .......... *C07D493/06* (2013.01); *C07D 495/06* (2013.01); *C09B 5/62* (2013.01); *H01G 9/2059* (2013.01); *H01L 51/006* (2013.01); *H01L 51/0053* (2013.01); *H01L 51/0061* (2013.01); *H01G 9/2031* (2013.01); *H01L 51/4226* (2013.01); *Y02E 10/542* (2013.01); *Y02E 10/549* (2013.01); *Y02P 70/521* (2015.11)

(56) References Cited

U.S. PATENT DOCUMENTS

| | | | |
|---|---|---|---|
| 5,350,644 | A | 9/1994 | Graetzel et al. |
| 8,816,081 | B2 | 8/2014 | Wonneberger et al. |
| 9,054,325 | B2 | 6/2015 | Benedito et al. |
| 9,062,207 | B2 * | 6/2015 | Pasquier .................. C09B 5/62 |
| 9,105,410 | B2 | 8/2015 | Wonneberger et al. |
| 2006/0078518 | A1 | 4/2006 | Elder et al. |
| 2008/0269482 | A1 | 10/2008 | Pschirer et al. |
| 2015/0179954 | A1 | 6/2015 | Gessner et al. |
| 2015/0225413 | A1 | 8/2015 | Wonneberger et al. |
| 2015/0225418 | A1 | 8/2015 | Gessner et al. |
| 2015/0284569 | A1 | 10/2015 | Wonneberger et al. |

FOREIGN PATENT DOCUMENTS

| | | | |
|---|---|---|---|
| EP | 1 176 646 A1 | 1/2002 | |
| GB | 1 440 450 A | 6/1976 | |
| JP | 10-189065 | 7/1998 | |
| JP | 10-334954 | 12/1998 | |
| JP | 2000-100484 | 4/2000 | |
| JP | 2000-423463 | 9/2000 | |
| JP | 2001-93589 | 4/2001 | |
| JP | 2004-227825 A * | 8/2004 | ............. H01L 31/04 |
| WO | WO 2006/021527 A1 | 3/2006 | |
| WO | 2007/054470 A1 | 5/2007 | |
| WO | WO 2012/001628 A1 | 1/2012 | |

OTHER PUBLICATIONS

International Preliminary Report on Patentability and Written Opinion issued Sep. 22, 2015 in corresponding PCT/IB2014/059678 filed Mar. 12, 2014.
Nature, Letters to Nature, 1991, vol. 353, pp. 737-740.
U. Bach, et al., Solid-state dye-sensitized mesoporous $TiO_2$ solar cells with high photon-to-electron conversion efficiencies Nature, Letters to Nature, Oct. 1998, vol. 395, pp. 583-585.
Mohammad K. Nazeeruddin et al., "Combined Experimental and DFT-TDDFT Computational Study of Photoelectrochemical Cell Ruthenium Sensitizers", J. Am. Chem. Soc., 2005, vol. 127, pp. 16835-16847.
Yasuo Chiba et al., "Dye-Sensitized Solar Cells with Conversion Efficiency of 11.1%", Japanese Journal of Applied Physics, 2006, vol. 45, No. 25, pp. L638-L640.
Feifei Gao et al., "Enhance the Optical Absorptivity of Nanocrystalline TiO2 Film with High Molar Extinction Coefficient Ruthenium Sensitizers for High Performance Dye-Sensitized Solar Cells", J. Am. Chem. Soc., 2008, vol. 130, pp. 10720-10728.
Yiming Cao et al., "Dye-Sensitized Solar Cells with a High Absorptivity Ruthenium Sensitizer Featuring a 2-(Hexylthio)thiophene Conjugated Bipyridine", J. Phys. Chem. C, 2009, vol. 113, pp. 6290-6297.
Chia-Yuan Chen et al., "Highly Efficient Light-Harvesting Ruthenium Sensitizer for Thin-Film Dye-Sensitized Solar Cells ACS Nano", 2009, vol. 3, No. 10, pp. 3103-3109.
Gopal K. Mor et al., Visible to Near-Infrared Light Harvesting in $TiO_2$ Nanotube Array-P3HT Based Heterojunction Solar Cells Nano Lett., 2009, vol. 9, No. 12, pp. 4250-4257.
Henry J. Snaith, et al., "Efficiency Enhancements in Solid-State Hybrid Solar Cells via Reduced Charge Recombination and Increased Light Capture", Nano Lett., 2007, vol. 7, No. 11, pp. 3372-3376.
Suzanne Ferrere, et al., "New perylenes for dye sensitization of $TiO_2$", New J. Chem., 2002, vol. 26, pp. 1155-1160.
Xuhong Qianet, al., "Intramolecular aromatic 1,5-hydrogen transfer in preparation of oxacyclic naphthalic anhydride via unusual Pschorr cyclisation", Chemcomm Communication, 2001, pp. 2656-2657.
Hong Yin, et al., "Novel aliphatic N-oxide of naphthalimides as fluorescent markers for hypoxic cells in solid tumor", European Journal of Medicinal Chemistry, 2011, vol. 46, pp. 3030-3037.
P. H. Grayshan et al., "Heterocyclic Derivatives of Naphthalene-I,8-dicarboxylie Anhydride. Part III. (I) Benzo[*k,l*] thioxanthene-3,4-dicarboximides" Heterocyclic Chem., 1974, pp. 34-38.
Qian Xuhong, et al., Benzoxanthene-3,4-dicarboximides and Benzimidazoxanthenoisoquinolinones, J. Chem. Eng. Data, 1988, vol. 33, pp. 528-529.
Qing Yang, et al., "Thio-heterocylic naphthalimides with aminoalkyl side chains:novel alternative tools for photodegradation of genomic DNA without impairment on bioactivities of proteins", Bioorganic & Medicinal Chemistry, 2005, vol. 13, pp. 1615-1622.
Qing Yang, et al., Naphthalimide intercalators with chiral amino side chains: Effects of chirality on DNA binding, photodamage and antitumor cytotoxicity Bioorganic & Medicinal Chemistry Letters, 2008, vol. 18, pp. 6210-6213.
A. M. Kadhim, et al., "A New intramolecular Cyslisation Reaction-I Novel Synthesis of Benzo(k,l) Thioxanthene-3-4-Dicarboxylic Anhydride and Derived Dyestuffs", 1974, vol. 30, pp. 2245-2249.
Qian Xuhong et al., "Highly-efficient DNA photocleavers with long wavelength absorptions: thio-heterocyclic fused naphthalimides containing aminoalkyl side chains", Bioorganic & Medicinal Chemistry Letters, 2004, vol. 14, pp. 2665-2668.
Henrike Wonneberger, et al., "Double Donor-Thiophene Dendron-Perylene Monoimide: Efficient Light-Harvesting Metal-Free Chromophore for Solid-State Dye-Sensitized Solar Cells", Chemistry—An Asian Journal, 2011, vol. 6, pp. 1744-1747.
Bin Peng, et al., "Systematic investigation of the role of compact TiO2 layer in solid state dye-sensitized TiO2 solar Cells", Coordination Chemistry Reviews, 2004, vol. 248, pp. 1479.
Eiichi Miyamoto et al., "Ionization Potential of Organic Pigment Film by Atmospheric Photoelectron Emission Analysis", Electrophotography, 1989, vol. 28, pp. 364-370 (with partial English translation).
M. Cordona et al., Topics in Applied Physics, Introduction, 1978, vol. 26, 55 Pages.
Qian Xu Hong et al., "Fluorecent Dyes for Solar Cells of 1, 8-Naphthalic Anhydride Photographic science and Photochemistry", Photographic science and photochemistry, 1989, Issue 4, 6 Pages.
Qian Xuhong et al., "A study on the relationship between stoke's shift and low frequency half-value component of fluorescent compounds", Dyes and Pigments, 1996, vol. 32, Issue 4, 7 Pages.
Martin Danko et al, "Photochemical stability and photo-stabilizing efficiency of probes based on benzothioxanthene chromophore and hindered amine stabilizer", Polymer Degradation and Stability, Synthesis, 2006, Issue 91, pp. 1045-1051.

* cited by examiner

PERYLENEMONOIMIDE AND NAPHTHALENEMONOIMIDE DERIVATIVES AND THEIR USE IN DYE-SENSITIZED SOLAR CELLS

The present invention relates to the use of compounds of general formula I

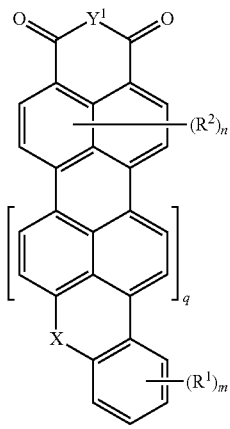

(I)

wherein the variables have the following meaning
$R^1$, $R^2$ independently of each other hydrogen, halogen, alkyl, cycloalkyl, aryl, hetaryl, alkoxy, aryloxy, arylthio, hetaryloxy, hetarylthio, diarylamino or dialkylamino,
m, n independently of each other 0, 1, 2, 3 or 4,
q 0 or 1,
X sulfur, oxygen or $NR^3$,
$R^3$ hydrogen, alkyl, cycloalkyl, aryl or hetaryl,
$Y^1$ oxygen or N—Z-A,
A is —COOM, —$SO_3$M or —$PO_3$M,
M hydrogen, alkali metal cation or $[NR']^{4+}$,
R' hydrogen or alkyl, where the radicals R' may be identical or different,
Z $C_1$-$C_6$-alkylene or 1,4-phenylene, where the phenylene radical may be substituted by one or more substituents alkyl, nitro, cyano and/or halogen,
in dye-sensitized solar cells;
to compounds of general formula I'

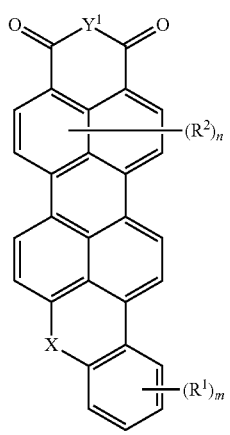

(I')

wherein the variables have the following meaning
$R^1$, $R^2$ independently of each other hydrogen, halogen, alkyl, cycloalkyl, aryl, hetaryl, alkoxy, aryloxy, arylthio, hetaryloxy, hetarylthio, diarylamino or dialkylamino,
m, n independently of each other 0, 1, 2, 3 or 4,
X sulfur, oxygen or $NR^3$,
$R^3$ hydrogen, alkyl, cycloalkyl, aryl or hetaryl,
$Y^1$ oxygen or N—Z-A,
A is —COOM, —$SO_3$M or —$PO_3$M,
M hydrogen, alkali metal cation or $[NR']^{4+}$,
R' hydrogen or alkyl, where the radicals R' may be identical or different,
Z $C_1$-$C_6$-alkylene or 1,4-phenylene, where the phenylene radical may be substituted by one or more substituents alkyl, nitro, cyano and/or halogen;
to compounds of general formula I"

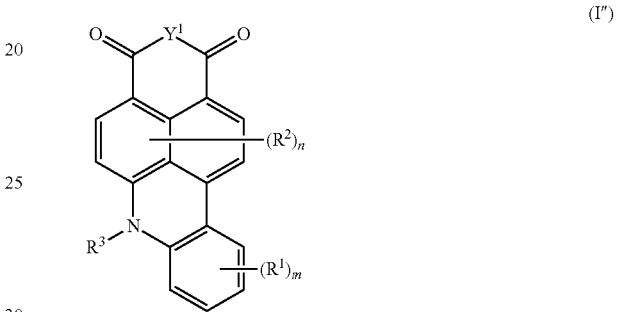

(I")

wherein the variables have the following meaning
$R^1$, $R^2$ independently of each other hydrogen, halogen, alkyl, cycloalkyl, aryl, hetaryl, alkoxy, aryloxy, arylthio, hetaryloxy, hetarylthio, diarylamino or dialkylamino,
m, n independently of each other 0, 1, 2, 3 or 4,
$R^3$ hydrogen, alkyl, cycloalkyl, aryl or hetaryl,
$Y^1$ oxygen or N—Z-A,
A is —COOM, —$SO_3$M or —$PO_3$M,
M hydrogen, alkali metal cation or $[NR']^{4+}$,
R' hydrogen or alkyl, where the radicals R' may be identical or different,
Z $C_1$-$C_6$-alkylene or 1,4-phenylene, where the phenylene radical may be substituted by one or more substituents alkyl, nitro, cyano and/or halogen;
to the use of compounds of general formula II

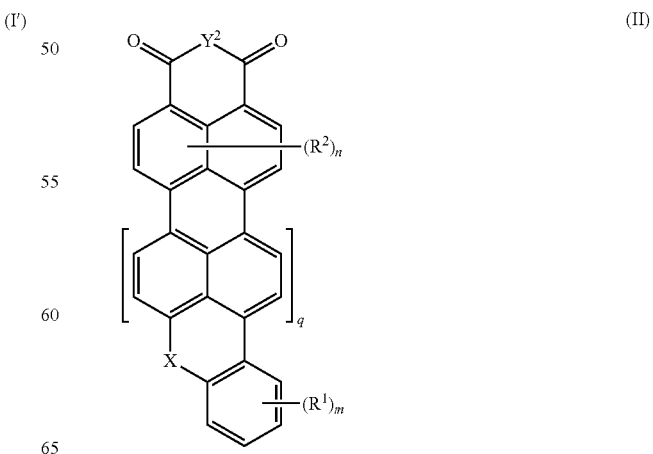

(II)

wherein the variables have the following meaning
R¹, R² independently of each other hydrogen, halogen, alkyl, cycloalkyl, aryl, hetaryl, alkoxy, aryloxy, arylthio, hetaryloxy, hetarylthio, diarylamino or dialkylamino,
m, n independently of each other 0, 1, 2, 3 or 4,
q 0 or 1,
X sulfur, oxygen or NR³,
R³ hydrogen, alkyl, cycloalkyl, aryl or hetaryl,
Y² NR⁴,
R⁴ hydrogen, alkyl, cycloalkyl, aryl or hetaryl,
in the case of q equal to 0 or 1:
as precursor compounds for the manufacture of compounds of general formula I and
in the case of q equal to 1:
as precursor compounds for the manufacture of compounds of general formula I';
to compounds of general formula III

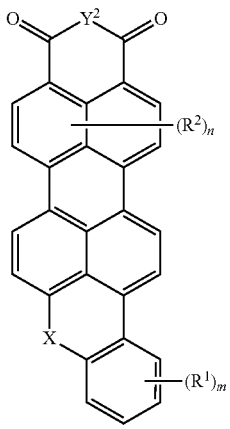

wherein the variables have the following meaning
R¹, R² independently of each other hydrogen, halogen, alkyl, cycloalkyl, aryl, hetaryl, alkoxy, aryloxy, arylthio, hetaryloxy, hetarylthio, diarylamino or dialkylamino,
m, n independently of each other 0, 1, 2, 3 or 4,
X sulfur, oxygen or NR³,
R³ hydrogen, alkyl, cycloalkyl, aryl or hetaryl,
Y² NR⁴,
R⁴ hydrogen, alkyl, cycloalkyl, aryl or hetaryl;
to the use of compounds of general formulae I, I' or I" as sensitizers in dye-sensitized solar cells;
and to such dye-sensitized solar cells per se.

The direct conversion of solar energy to electrical energy in solar cells is based on the internal photoeffect of a semiconductor material, i.e. the generation of electron-hole pairs by absorption of photons and the separation of the negative and positive charge carriers at a p-n junction or a Schottky contact. The photovoltage thus generated can bring about a photocurrent in an external circuit, through which the solar cell delivers its power.

Thin layers or films of metal oxides are known to constitute inexpensive solid semiconductor materials (n-semiconductors), but their absorption, owing to large band gaps, is typically not within the visible region of the electromagnetic spectrum. For use in solar cells, the metal oxides therefore have to be combined with a photosensitizer which absorbs in the wavelength range of sunlight, i.e. at from 300 to 2000 nm, and, in the electronically excited state, injects electrons into the conduction band of the semiconductor. With the aid of a redox system which is used additionally in the cell and is reduced at the counterelectrode, electrons are recycled to the sensitizer which is thus regenerated.

Of particular interest for use in solar cells are the semiconductors zinc oxide, tin dioxide and especially titanium dioxide, which are used in the form of nanocrystalline porous layers. These layers have a large surface area which is coated with the sensitizer, so that high absorption of sunlight is achieved.

Dye-sensitized solar cells (DSCs) which are based on titanium dioxide as the semiconductor material are described, for example, in U.S. Pat. No. 4,927,721, Nature 353, p. 737-740 (1991) and U.S. Pat. No. 5,350,644, and also Nature 395, p. 583-585 (1998) and EP-A-1 176 646. These solar cells comprise monomolecular films of transition metal complexes, especially ruthenium complexes, which are bonded to the titanium dioxide layer via acid groups, as sensitizers and iodine/iodide redox systems present in dissolved form or amorphous organic p-conductors based on spirobifluorenes.

Ruthenium complexes as molecular sensitizers have shown impressive solar-to-electric power conversion efficiencies (PCE) in liquid electrolyte based devices, with the PCE reaching over 11% under standard AM 1.5G full sunlight as was shown by M. K. Nazeeruddin, F. De Angelis, S. Fantacci, A. Selloni, G. Viscardi, P. Liska, S. Ito, T. Bessho, M. Grätzel, J. Am. Chem. Soc. 2005, 127, 16835;

Y. Chiba, A. Islam, Y. Watanabe, R. Komiya, N. Koide, L. Y. Han, Jpn. J. Appl. Phys. 2006, 45, L638;

F. Gao, Y. Wang, D. Shi, J. Zhang, M. K. Wang, X. Y. Jing, R. Humphry-Baker, P. Wang, S. M. Zakeeruddin, M. Grätzel, J. Am. Chem. Soc. 2008, 130, 10720;

Y. M. Cao, Y. Bai, Q. J. Yu, Y. M. Cheng, S. Liu, D. Shi, F. Gao, P. Wang, J. Phys. Chem. C 2009, 113, 6290; and C.-Y. Chen, M. K. Wang, J.-Y. Li, N. Pootrakulchote, L. Alibabaei, C. H. Ngoc-le, J. D. Decoppet, J. H. Tsai, C. Gratzel, C. G. Wu, S. M. Zakeeruddin, M. Grätzel, ACS Nano 2009, 3, 3103.

In recent years, metal-free organic dyes have attracted increasing attention as they do not contain any toxic or costly metal and their properties are easily tuned by facile structural modification. In addition, they generally have much higher extinction coefficients when compared to Ru(II) polypyridyls, making them excellent for use in solid state DSCs in combination with hole transporting materials such as P3HT as shown, for example, by G. K. Mor, S. Kim, M. Paulose, O. K. Varghese, K. Shankar, J. Basham and C. A. Grimes, Nano Lett., 2009, 9, 4250, or spiro-MeOTAD as shown, for example, by H. J. Snaith, A. J. Moule, C. Klein, K. Meerholz, R. H. Friend, M. Grätzel, Nano Lett., 2007, 7, 3372.

Due to their high extinction coefficients and long-term stability against the action of oxygen and/or light rylene derivatives have attracted much attention as possible sensitizers for DSCs.

Thus, perylene-3,4:9,10-tetracarboxylic acid derivatives as sensitizers are examined in Japanese documents JP-A-10-189065, 2000-243463, 2001-093589, 2000-100484 and 10-334954, and in New J. Chem. 26, p. 1155-1160 (2002).

Further rylene derivatives useful as sensitizers in DSCs are prepared and evaluated in WO 2007/054470 A1.

In order to facilitate tailor-made adjustments of the molecular properties of rylenes, versatile substitution patterns are desirable. Rylene derivatives with core-extensions comprising heteroatoms like nitrogen, sulfur or oxygen, like compounds depicted in formula I at the outset, were hitherto not considered for use in organic electronics applications.

Naphthalene compounds of formula

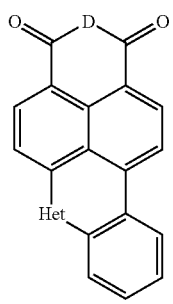

are described by X. Qian et al. in Chem. Commun., 2001, 2656-2657 (D=oxygen; Het=oxygen), in EP 1172418 A2 (D=N—(CH$_2$)$_6$—OH, Het=sulfur; D=N—(CH$_2$)$_6$—NH$_2$, Het=sulfur; D=N—(CH$_2$)$_2$—O—(CH$_2$)$_2$—O—(CH$_2$)$_2$—NH$_2$, Het=sulfur), by H. Yin et al. in European Journal of Medicinal Chemistry 46 (2011) 3030-2037 (D=N—(CH$_2$)$_2$—N(CH$_3$)$_2$, Het=sulfur; D=N—(CH$_2$)$_2$—N(CH$_3$)$_2$, Het=oxygen; D=oxygen, Het=oxygen; D=N—(CH$_2$)$_2$—N$^+$(O$^-$)(CH$_3$)$_2$, Het=sulfur; D=N—(CH$_2$)$_2$—N$^+$(O$^-$)(CH$_3$)$_2$, Het=oxygen), by P. H. Grayshan et al. in Heterocyclic Chem. 1974, 34-38 (D=N—R, Het=sulfur; D=oxygen, Het=sulfur), by Qian Xuhong and Ren Shengwu in J. Chem. Eng. Data 1988, 33, 528-529 (D=oxygen, Het=oxygen; D=NR, Het=oxygen), by Q. Yang et al. in Bioorg. Med. Chem. 13 (2005) 1615-1622 (D=oxygen, Het=sulfur; D=NR, Het=sulfur), by Q. Yang et al. in Bioorganic & Medicinal Chemistry Letters 18 (2008) 6210-6213 (D=NR, Het=sulfur; D=oxygen, Het=sulfur), by A. M. Kadhim and A. T. Peters in Tetrahedron. Vol. 30 (1974), 2245-2249 (D=oxygen, Het=sulfur; D=NR, Het=sulfur), by Qian Xuhong et al. in Tetrahedron Letters 43 (2002) 2995-2998 (D=oxygen, Het=sulfur; D=N—CH$_2$—CH=C(CH$_3$)$_2$, Het=sulfur; D=N—CH$_2$—CH(OOH)—C(CH$_3$)=CH$_2$)) and by Qian Xuhong et al. in Bioorganic & Medicinal Chemistry Letters 14 (2004) 2665-2668 (D=NR, Het=sulfur). Those compounds were reported for use in biochemical DNA cleavage reactions, as fluorescent markers for biochemical purposes, as laser or textile dyes, organic pigments and organic whitening agents. None of those references refers to the use of those compounds in the field of organic electronics.

It is the main object of the present invention to provide further rylene compounds the optical and electronic properties of which can be easily tuned for various organic electronics applications, e. g. in the field of organic photovoltaics.

Accordingly, compounds of general formula I

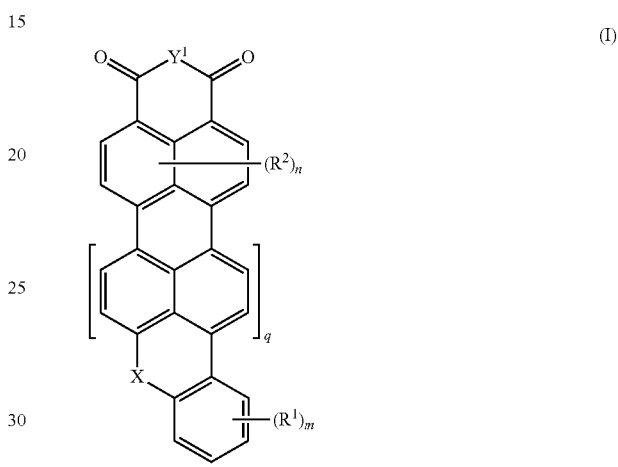

have been found for use in dye-sensitized colar cells, wherein the variables have the following meaning R$^1$, R$^2$ independently of each other hydrogen, halogen, alkyl, cycloalkyl, aryl, hetaryl, alkoxy, aryloxy, arylthio, hetaryloxy, hetarylthio, diarylamino or dialkylamino, m, n independently of each other 0, 1, 2, 3 or 4, q 0 or 1, X sulfur, oxygen or NR$^3$, R$^3$ hydrogen, alkyl, cycloalkyl, aryl or hetaryl, Y$^1$ oxygen or N—Z-A, A is —COOM, —SO$_3$M or —PO$_3$M, M hydrogen, alkali metal cation or [NR']$^{4+}$, R' hydrogen or alkyl, where the radicals R' may be identical or different, and Z C$_1$-C$_6$-alkylene or 1,4-phenylene, where the phenylene radical may be substituted by one or more substituents alkyl, nitro, cyano and/or halogen.

Preferred use is made of compounds wherein in general formula I the variables have the following meaning R$^1$, R$^2$ independently of each other hydrogen, halogen, aryl, aryloxy, arylthio, hetaryloxy, hetarylthio or dialkylamino, m, n independently of each other 0, 1 or 2, q 0 or 1, X sulfur, oxygen or NR$^3$, R$^3$ alkyl or aryl, Y$^1$ oxygen or N—Z-A, A is —COOM, M hydrogen, alkali metal cation or [NR']$^{4+}$, R' hydrogen or alkyl, where the radicals R' may be identical or different, and Z C$_1$-C$_6$-alkylene or 1,4-phenylene.

A further objective of the instant invention are compounds of general formula I'

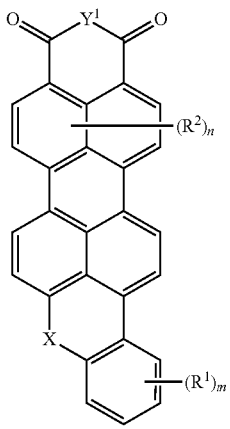

(I')

wherein the variables have the following meaning
R¹, R² independently of each other hydrogen, halogen, alkyl, cycloalkyl, aryl, hetaryl, alkoxy, aryloxy, arylthio, hetaryloxy, hetarylthio, diarylamino or dialkylamino,
m, n independently of each other 0, 1, 2, 3 or 4,
X sulfur, oxygen or $NR^3$,
$R^3$ hydrogen, alkyl, cycloalkyl, aryl or hetaryl,
$Y^1$ oxygen or N—Z-A,
A is —COOM, —$SO_3$M or —$PO_3$M,
M hydrogen, alkali metal cation or $[NR']^{4+}$,
R' hydrogen or alkyl, where the radicals R' may be identical or different and
Z $C_1$-$C_6$-alkylene or 1,4-phenylene, where the phenylene radical may be substituted by one or more substituents alkyl, nitro, cyano and/or halogen.

The variables of preferred compounds of general formula I' have the following meaning
R¹, R² independently of each other hydrogen, halogen, aryl, aryloxy, arylthio, hetaryloxy, hetarylthio or dialkylamino,
m, n independently of each other 0, 1 or 2,
X sulfur, oxygen or $NR^3$,
$R^3$ alkyl or aryl,
$Y^1$ oxygen or N—Z-A,
A —COOM,
M hydrogen, alkali metal cation or $[NR']^{4+}$,
R' hydrogen or alkyl, where the radicals R' may be identical or different and
Z $C_1$-$C_6$-alkylene or 1,4-phenylene.

A further objective of the instant invention are compounds of general formula I''

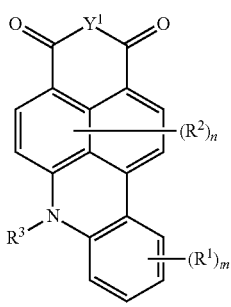

(I'')

wherein the variables have the following meaning
R¹, R² independently of each other hydrogen, halogen, alkyl, cycloalkyl, aryl, hetaryl, alkoxy, aryloxy, arylthio, hetaryloxy, hetarylthio, diarylamino or dialkylamino,
m, n independently of each other 0, 1, 2, 3 or 4,
$R^3$ hydrogen, alkyl, cycloalkyl, aryl or hetaryl,
$Y^1$ oxygen or N—Z-A,
A is —COOM, —$SO_3$M or —$PO_3$M,
M hydrogen, alkali metal cation or $[NR']^{4+}$,
R' hydrogen or alkyl, where the radicals R' may be identical or different and
Z $C_1$-$C_6$-alkylene or 1,4-phenylene, where the phenylene radical may be substituted by one or more substituents alkyl, nitro, cyano and/or halogen.

In preferred compounds of general formula I'' the variables have the following meaning
R¹, R² independently of each other hydrogen, halogen, aryl, aryloxy, arylthio, hetaryloxy, hetarylthio or dialkylamino,
m, n independently of each other 0, 1 or 2,
$R^3$ alkyl or aryl,
$Y^1$ oxygen or N—Z-A,
A —COOM,
M hydrogen, alkali metal cation or $[NR']^{4+}$,
R' hydrogen or alkyl, where the radicals R' may be identical or different and
Z $C_1$-$C_6$-alkylene or 1,4-phenylene.

A further objective of the instant invention is the use of compounds of general formula II

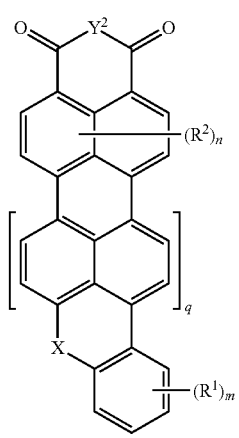

(II)

wherein the variables have the following meaning
R¹, R² independently of each other hydrogen, halogen, alkyl, cycloalkyl, aryl, hetaryl, alkoxy, aryloxy, arylthio, hetaryloxy, hetarylthio, diarylamino or dialkylamino,
m, n independently of each other 0, 1, 2, 3 or 4,
q 0 or 1,
X sulfur, oxygen or $NR^3$,
$R^3$ hydrogen, alkyl, cycloalkyl, aryl or hetaryl,
$Y^2$ $NR^4$ and
$R^4$ hydrogen, alkyl, cycloalkyl, aryl or hetaryl,
in the case of q equal to 0 or 1:
as precursor compounds for the manufacture of compounds of general formula I and
in the case of q equal to 1:
as precursor compounds for the manufacture of compounds of general formula I'.

Typically, compounds of general formula II can be submitted to treatment with an hydroxide alkaline reagent in a fairly or non-nucleophilic solvent or suspending agent to yield compounds of general formula i

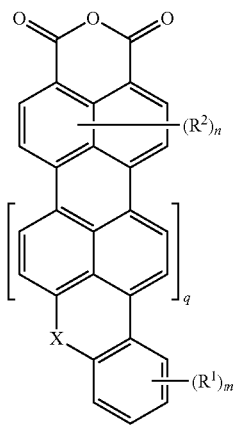

(i)

These latter compounds are identical to compounds of general formula I where $Y^1$ has the meaning of oxygen. Compounds of general formula i can be turned into compounds of general formula ii

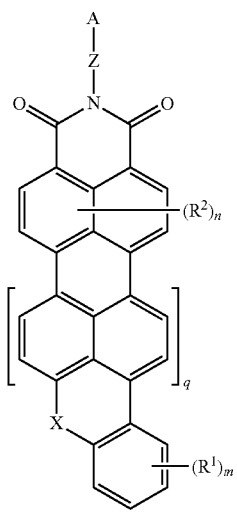

(ii)

by reacting compounds of general formula i with an amine of formula

H$_2$N—Z-A where Z and A have the meaning given in the definition of the variables of compounds of general formula I. Typically, the amination reaction is carried out with the aid of a water binding agent like, e.g. imidazole, in the presence of a polar aprotic solvent or supending agent, examples of which are given below. Reaction without solvent or suspending agent is also possible. This route is describe e.g. by H. Wonneberger et al. in Chemistry—An Asian Journal 2011, 6, 1744-1747.

Another route for the preparation of the compound of formula ii is the reaction of the compound of formula i with the aforementioned amine in an polar aprotic solvent in the presence of Lewis-acidic salts of organic or inorganic acids with metals such as zinc, iron, copper and magnesium and also the oxides of these metals, for example zinc acetate, zinc propionate, zinc oxide, iron(III) acetate, iron(II) chloride, iron(II) sulfate, copper(II) acetate, copper(II) oxide and magnesium acetate, particular preference being given to zinc acetate. The salts are preferably used in anhydrous form.

Suitable polar aprotic solvents for both aforementioned routes are in particular aprotic nitrogen heterocycles such as pyridine, pyrimidine, imidazole, quinoline, isoquinoline, N-methylpiperidine, N-methylpiperidone and N-methylpyrrolidone, or carboxamides such as dimethylformamide and dimethylacetamide. Further information on this route can be retrieved e.g. from US 2008/0269482 A1 from the passage starting on page 21 and titled "A.3. Preparation of Rylene Derivatives of the Formula Ia3".

Examples of reactions of compounds of general formula II to compounds of general formula i and further reaction of the latter to yield compounds of general formula ii are given in the experimental part.

According to the instant invention preferred use is made of compounds of general formula II'

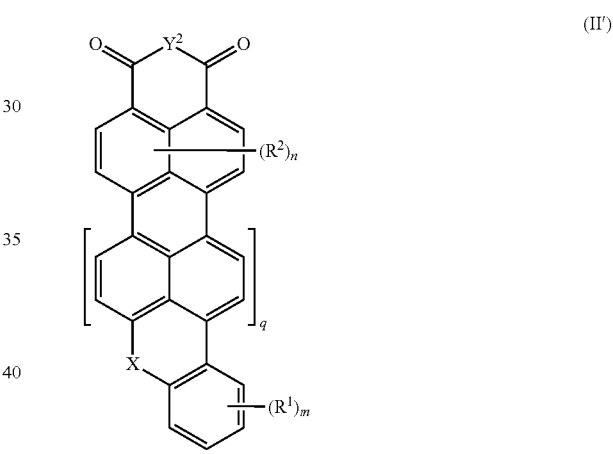

wherein the variables have the following meaning $R^1$, $R^2$ independently of each other hydrogen, halogen, aryl, aryloxy, arylthio, hetaryloxy, hetarylthio or dialkylamino, m, n independently of each other 0, 1 or 2, q 0 or 1, X sulfur, oxygen or NR$^3$, $R^3$ alkyl or aryl, $Y^2$ NR$^4$ and $R^4$ hydrogen, alkyl, cycloalkyl, aryl or hetaryl, in the case of q equal to 0 or 1:

as precursor compounds for the manufacture of compounds of general formula I according to their preferred embodiments and in the case of q equal to 1:

as precursor compounds for the manufacture of compounds of general formula I' according to their preferred embodiments.

A further objective of the instant invention are compounds of general formula III

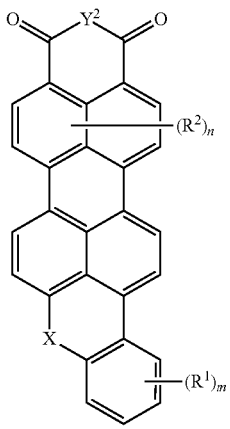

(III)

wherein the variables have the following meaning
$R^1$, $R^2$ independently of each other hydrogen, halogen, alkyl, cycloalkyl, aryl, hetaryl, alkoxy, aryloxy, arylthio, hetaryloxy, hetarylthio, diarylamino or dialkylamino,
m, n independently of each other 0, 1, 2, 3 or 4,
X sulfur, oxygen or $NR^3$,
$R^3$ hydrogen, alkyl, cycloalkyl, aryl or hetaryl,
$Y^2$ $NR^4$,
$R^4$ hydrogen, alkyl, cycloalkyl, aryl or hetaryl.

In preferred compounds of general formula III the variables have the following meaning
$R^1$, $R^2$ independently of each other hydrogen, halogen, aryl, aryloxy, arylthio, hetaryloxy, hetarylthio or dialkylamino,
m, n independently of each other 0, 1 or 2,
X sulfur, oxygen or $NR^3$,
$R^3$ alkyl or aryl,
$Y^2$ $NR^4$ and
$R^4$ hydrogen, alkyl, cycloalkyl, aryl or hetaryl.

In preferred compounds of general formula III according to the instant invention the variables have the following meaning
$R^1$, $R^2$ independently of each other hydrogen, halogen, aryl, aryloxy, arylthio, hetaryloxy, hetarylthio or dialkylamino,
m, n independently of each other 0, 1 or 2,
X $NR^3$,
$R^3$ alkyl or aryl,
$Y^2$ $NR^4$ and
$R^4$ hydrogen, alkyl, cycloalkyl, aryl or hetaryl.

A further objective of the instant invention is the use of compounds of general formula I and preferred compounds of general formula I as sensitizers in dye-sensitized solar cells.

A further objective of the instant invention is the use of compounds of general formula I' and preferred compounds of general formula I' as sensitizers in dye-sensitized solar cells.

A further objective of the instant invention is the use of compounds of general formula I" and preferred compounds of general formula I'" as sensitizers in dye-sensitized solar cells.

A further objective of the instant invention is a dye-sensitized solar cell comprising compounds of general formula I and preferred compounds of general formula I.

A further objective of the instant invention is a dye-sensitized solar cell comprising compounds of general formula I' and preferred compounds of general formula I'.

A further objective of the instant invention is a dye-sensitized solar cell comprising compounds of general formula I" and preferred compounds of general formula I".

In the context of the present invention, alkyl, aryl or heteroaryl represents unsubstituted or substituted alkyl, unsubstituted or substituted aryl or unsubstituted or substituted heteroaryl.

Alkyl comprises straight-chain or branched alkyl. Alkyl is preferably $C_1$-$C_{30}$-alkyl, especially $C_1$-$C_{20}$-alkyl and most preferably $C_1$-$C_{12}$-alkyl. Examples of alkyl groups are especially methyl, ethyl, n-propyl, isopropyl, n-butyl, isobutyl, sec-butyl, tert-butyl, n-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl.

Further examples of branched alkyl groups can be represented by the following formula

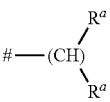

in which
# denotes a bonding site, and
$R^a$ is selected from $C_1$- to $C_{28}$-alkyl, where the sum of the carbon atoms of the
$R^g$ radicals is an integer from 2 to 29.

In the formula above, the $R^a$ radicals are preferably selected from $C_1$- to $C_{12}$-alkyl, especially $C_1$- to $C_8$-alkyl.

Preferred branched alkyl radicals of the above formula are, for example:
1-ethylpropyl, 1-methylpropyl, 1-propylbutyl, 1-ethylbutyl, 1-methylbutyl, 1-butylpentyl, 1-propylpentyl, 1-ethylpentyl, 1-methylpentyl, 1-pentylhexyl, 1-butylhexyl, 1-propylhexyl, 1-ethylhexyl, 1-methylhexyl, 1-hexylheptyl, 1-pentylheptyl, 1-butylheptyl, 1-propylheptyl, 1-ethylheptyl, 1-methylheptyl, 1-heptyloctyl, 1-hexyloctyl, 1-pentyloctyl, 1-butyloctyl, 1-propyloctyl, 1-ethyloctyl, 1-methyloctyl, 1-octylnonyl, 1-heptylnonyl, 1-hexylnonyl, 1-pentylnonyl, 1-butylnonyl, 1-propylnonyl, 1-ethylnonyl, 1-methylnonyl, 1-nonyldecyl, 1-octyldecyl, 1-heptyldecyl, 1-hexyldecyl, 1-pentyldecyl, 1-butyldecyl, 1-propyldecyl, 1-ethyldecyl, 1-methyldecyl, 1-decylundecyl, 1-nonylundecyl, 1-octylundecyl, 1-heptylundecyl, 1-hexylundecyl, 1-pentylundecyl, 1-butylundecyl, 1-propylundecyl, 1-ethylundecyl, 1-methylundecyl, 1-undecyldodecyl, 1-decyldodecyl, 1-nonyldodecyl, 1-octyldodecyl, 1-heptyldodecyl, 1-hexyldodecyl, 1-pentyldodecyl, 1-butyldodecyl, 1-propyldodecyl, 1-ethyldodecyl, 1-methyldodecyl, 1-dodecyltridecyl, 1-undecyltridecyl, 1-decyltridecyl, 1-nonyltridecyl, 1-octyltridecyl, 1-heptyltridecyl, 1-hexyltridecyl, 1-pentyltridecyl, 1-butyltridecyl, 1-propyltridecyl, 1-ethyltridecyl, 1-methyltridecyl, 1-tridecyltetradecyl, 1-undecyltetradecyl, 1-decyltetradecyl, 1-nonyltetradecyl, 1-octyltetradecyl, 1-heptyltetradecyl, 1-hexyltetradecyl, 1-pentyltetradecyl, 1-butyltetradecyl, 1-propyltetradecyl, 1-ethyltetradecyl, 1-methyltetradecyl, 1-pentadecylhexadecyl, 1-tetradecylhexadecyl, 1-tridecylhexadecyl, 1-dodecylhexadecyl, 1-undecylhexadecyl, 1-decylhexadecyl, 1-nonylhexadecyl, 1-octylhexadecyl, 1-heptylhexadecyl, 1-hexylhexadecyl, 1-pentylhexadecyl, 1-butylhexadecyl, 1-propylhexadecyl, 1-ethylhexadecyl, 1-methylhexadecyl, 1-hexadecyloctadecyl, 1-pentadecyloctadecyl, 1-tetradecyloctadecyl, 1-tridecyloctadecyl, 1-dodecyloctadecyl, 1-undecyloctadecyl, 1-decyloctadecyl, 1-nonyloctadecyl, 1-octyloctadecyl, 1-heptyloctadecyl, 1-hexyloctadecyl, 1-pentyloctadecyl, 1-butyloctadecyl, 1-propyloctadecyl, 1-ethyloctadecyl, 1-methyloctadecyl, 1-nonadecyleicosanyl, 1-octadecyleicosanyl, 1-heptadecyleicosanyl, 1-hexadecyleicosanyl, 1-pentadecyleicosanyl, 1-tetradecyleicosanyl, 1-tridecyleicosanyl, 1-dodecyleicosanyl, 1-undecyleicosanyl, 1-decyleicosanyl, 1-nonyleicosanyl, 1-octyleicosanyl, 1-heptyleicosanyl, 1-hexyleicosanyl, 1-pentyleicosanyl, 1-butyleicosanyl, 1-propyleicosanyl, 1-ethyleicosanyl, 1-methyleicosanyl, 1-eicosanyldocosanyl, 1-nonadecyldocosanyl, 1-octadecyldocosanyl, 1-heptadecyldocosanyl, 1-hexadecyldocosanyl, 1-pentadecyldocosanyl, 1-tetradecyldocosanyl, 1-tridecyldocosanyl, 1-undecyldocosanyl, 1-decyldocosanyl, 1-nonyldocosanyl, 1-octyldocosanyl, 1-heptyldocosanyl, 1-hexyldocosanyl, 1-pentyldocosanyl, 1-butyldocosanyl, 1-propyldocosanyl, 1-ethyldocosanyl, 1-methyldocosanyl, 1-tricosanyltetracosanyl, 1-docosanyltetracosanyl, 1-nonadecyltetracosanyl, 1-octadecyltetracosanyl, 1-heptadecyltetracosanyl, 1-hexadecyltetracosanyl, 1-pentadecyltetracosanyl, 1-pentadecyltetracosanyl, 1-tetradecyltetracosanyl, 1-tridecyltetracosanyl, 1-dodecyltetracosanyl, 1-undecyltetracosanyl, 1-decyltetracosanyl, 1-nonyltetracosanyl, 1-octyltetracosanyl, 1-heptyltetracosanyl, 1-hexyltetracosanyl, 1-pentyltetracosanyl, 1-butyltetracosanyl, 1-propyltetracosanyl, 1-ethyltetracosanyl, 1-methyltetracosanyl, 1-heptacosanyloctacosanyl, 1-hexacosanyloctacosanyl, 1-pentacosanyloctacosanyl, 1-tetracosanyloctacosanyl, 1-tricosanyloctacosanyl, 1-docosanyloctacosanyl, 1-nonadecyloctacosanyl, 1-octadecyloctacosanyl, 1-heptadecyloctacosanyl, 1-hexadecyloctacosanyl, 1-hexadecyloctacosanyl, 1-pentadecyloctacosanyl, 1-tetradecyloctacosanyl, 1-tridecyloctacosanyl, 1-dodecyloctacosanyl, 1-undecyloctacosanyl, 1-decyloctacosanyl, 1-nonyloctacosanyl, 1-octyloctacosanyl, 1-heptyloctacosanyl, 1-hexyloctacosanyl, 1-pentyloctacosanyl, 1-butyloctacosanyl, 1-propyloctacosanyl, 1-ethyloctacosanyl, 1-methyloctacosanyl.

Alkyl also comprises alkyl radicals whose carbon chains may be interrupted by one or more nonadjacent groups selected from oxygen, sulfur, —CO—, —NR$^b$—, —SO— and/or —SO$_2$— where R$^b$ is preferably hydrogen, unsubstituted straight-chain or branched alkyl as described before or unsubstituted aryl as described below.

Substituted alkyl groups may, depending on the length of the alkyl chain, have one or more (e.g. 1, 2, 3, 4, 5 or more than 5) substituents. These are preferably each independently selected from cycloalkyl, heterocycloalkyl, aryl, hetaryl, fluorine, chlorine, bromine, cyano and nitro.

Aryl-substituted alkyl radicals (aralkyl) have at least one unsubstituted or substituted aryl group, as defined below. The alkyl group of the aralkyl radical may bear at least one further substituent and/or be interrupted by one or more nonadjacent groups selected from oxygen, sulfur, —CO—, —NR$^b$—, —SO— and/or —SO$_2$— where R$^b$ is preferably hydrogen, unsubstituted straight-chain or branched alkyl as described before or unsubstituted aryl as described below. Arylalkyl is preferably phenyl-$C_1$-$C_{10}$-alkyl, more preferably phenyl-$C_1$-$C_4$-alkyl, for example benzyl, 1-phenethyl, 2-phenethyl, 1-phenprop-1-yl, 2-phenprop-1-yl, 3-phenprop-1-yl, 1-phenbut-1-yl, 2-phenbut-1-yl, 3-phenbut-1-yl, 4-phenbut-1-yl, 1-phenbut-2-yl, 2-phenbut-2-yl, 3-phenbut-2-yl, 4-phenbut-2-yl, 1-(phenmeth)eth-1-yl, 1-(phenmethyl)-1-(methyl)eth-1-yl or -(phenmethyl)-1-(methyl)prop-1-yl; preferably benzyl and 2-phenethyl.

Halogen-substituted alkyl groups (haloalkyl) comprise a straight-chain or branched alkyl group in which at least one hydrogen atom or all hydrogen atoms are replaced by halogen. The halogen atoms are preferably selected from fluorine, chlorine and bromine, especially fluorine and chlorine. Examples of haloalkyl groups are especially chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, —CH$_2$—C$_2$F$_5$, —CF$_2$—C$_2$F$_5$, —CF(CF$_3$)$_2$, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 5-fluoro-1-pentyl, 5-chloro-1-pentyl, 5-bromo-1-pentyl, 5-iodo-1-pentyl, 5,5,5-trichloro-1-pentyl, undecafluoropentyl, 6-fluoro-1-hexyl, 6-chloro-1-hexyl, 6-bromo-1-hexyl, 6-iodo-1-hexyl, 6,6,6-trichloro-1-hexyl or dodecafluorohexyl.

The above remarks regarding unsubstituted or substituted alkyl also apply to unsubstituted or substituted alkoxy and unsubstituted or substituted dialkylamino.

Specific examples of unsubstituted and substituted alkyl radicals which may be interrupted by one or more nonadjacent groups selected from oxygen, sulfur, —NR$^b$—, —CO—, —SO— and/or —SO$_2$— are:

methyl, ethyl, n-propyl, isopropyl, n-butyl, isobutyl, sec-butyl, tert-butyl, n-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl, 2-methoxyethyl, 2-ethoxyethyl, 2-propoxyethyl, 2-butoxyethyl, 3-methoxypropyl, 3-ethoxypropyl, 3-propoxypropyl, 3-butoxypropyl, 4-methoxybutyl, 4-ethoxybutyl, 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxatridecyl and 3,6,9,12-tetraoxatetradecyl;

2-methylthioethyl, 2-ethylthioethyl, 2-propylthioethyl, 2-butylthioethyl, 3-methylthiopropyl, 3-ethylthiopropyl, 3-propylthiopropyl, 3-butylthiopropyl, 4-methylthiobutyl, 4-ethylthiobutyl, 4-propylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiatridecyl and 3,6,9,12-tetrathiatetradecyl;

2-monomethyl- and 2-monoethylaminoethyl, 2-dimethylaminoethyl, 2- and 3-dimethylaminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-tri methyl-3,6,9-triazadecyl, 3,6,9-triazaundecyl, 3,6,9-trimethyl-3,6,9-triazaundecyl, 12-methyl-3,6,9,12-tetraazatridecyl and 3,6,9,12-tetramethyl-3,6,9,12-tetraazatridecyl;

(1-ethylethylidene)aminoethylene, (1-ethylethylidene)aminopropylene, (1-ethylethylidene)aminobutylene, (1-ethylethylidene)aminodecylene and (1-ethylethylidene)aminododecylene;

propan-2-on-1-yl, butan-3-on-1-yl, butan-3-on-2-yl and 2-ethylpentan-3-on-1-yl;

2-methylsulfinylethyl, 2-ethylsulfinylethyl, 2-propylsulfinylethyl, 2-isopropylsulfinylethyl, 2-butylsulfinylethyl, 2- and 3-methylsulfinylpropyl, 2- and 3-ethylsulfinylpropyl, 2- and 3-propylsulfinylpropyl, 2- and 3-butylsulfinylpropyl, 2- and 4-methylsulfinylbutyl, 2- and 4-ethylsulfinylbutyl, 2- and 4-propylsulfinylbutyl and 4-butylsulfinylbutyl;

2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylproypl, 2- and 4-methylsulfonylbutyl, 2- and 4-ethylsulfonylbutyl, 2- and 4-propylsulfonylbutyl and 4-butylsulfonylbutyl;

carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxyltetradecyl;

sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl;

2-hydroxyethyl, 2- and 3-hydroxypropyl, 3- and 4-hydroxybutyl and 8-hydroxyl-4-oxaoctyl;

2-cyanoethyl, 3-cyanopropyl, 3- and 4-cyanobutyl;

2-chloroethyl, 2- and 3-chloropropyl, 2-, 3- and 4-chlorobutyl, 2-bromoethyl, 2- and 3-bromopropyl and 2-, 3- and 4-bromobutyl;

2-nitroethyl, 2- and 3-nitropropyl and 2-, 3- and 4-nitrobutyl;

methoxy, ethoxy, propoxy, butoxy, pentoxy and hexoxy;

methylthio, ethylthio, propylthio, butylthio, pentylthio and hexylthio;

methylamino, ethylamino, propylamino, butylamino, pentylamino, hexylamino, dicyclopentylamino, dicyclohexylamino, dicycloheptylamino, diphenylamino and dibenzylamino;

formylamino, acetylamino, propionylamino and benzoylamino;

carbamoyl, methylaminocarbonyl, ethylaminocarbonyl, propylaminocarbonyl, butyl-aminocarbonyl, pentylaminocarbonyl, hexylaminocarbonyl, heptylaminocarbonyl, octylaminocarbonyl, nonylaminocarbonyl, decylaminocarbonyl and phenylamino-carbonyl;

aminosulfonyl, n-dodecylaminosulfonyl, N,N-diphenylaminosulfonyl, and N,N-bis(4-chlorophenyl)aminosulfonyl;

methoxycarbonyl, ethoxycarbonyl, propoxycarbonyl hexoxycarbonyl, dodecyloxycarbonyl, octadecyloxycarbonyl, phenoxycarbonyl, (4-tert-butyl phenoxy)carbonyl and (4-chlorophenoxy)carbonyl;

methoxysulfonyl, ethoxysulfonyl, propoxysulfonyl, butoxysulfonyl, hexoxysulfonyl, dodecyloxysulfonyl and octadecyloxysulfonyl.

In the context of the invention, cycloalkyl denotes a cycloaliphatic radical having preferably 3 to 10, more preferably 5 to 8, carbon atoms. Examples of cycloalkyl groups are especially cyclopropyl, cyclobutyl, cyclopentyl, cyclohexyl, cycloheptyl or cyclooctyl.

Substituted cycloalkyl groups may, depending on the ring size, have one or more (e.g. 1, 2, 3, 4, 5 or more than 5) substituents. These are preferably each independently selected from alkyl, alkoxy, alkylamino, alkylthio, cycloalkyl, heterocycloalkyl, aryl, hetaryl, fluorine, chlorine, bromine, cyano and nitro. In the case of substitution, the cycloalkyl groups preferably bear one or more, for example one, two, three, four or five, $C_1$-$C_6$-alkyl groups. Examples of substituted cycloalkyl groups are especially 2- and 3-methylcyclopentyl, 2- and 3-ethylcyclopentyl, 2-, 3- and 4-methylcyclohexyl, 2-, 3- and 4-ethylcyclohexyl, 2-, 3- and 4-propylcyclohexyl, 2-, 3- and 4-isopropylcyclohexyl, 2-, 3- and 4-butylcyclohexyl, 2-, 3- and 4-sec.-butylcyclohexyl, 2-, 3- and 4-tert-butylcyclohexyl, 2-, 3- and 4-methylcycloheptyl, 2-, 3- and 4-ethylcycloheptyl, 2-, 3- and 4-propylcycloheptyl, 2-, 3- and 4-isopropylcycloheptyl, 2-, 3- and 4-butylcycloheptyl, 2-, 3- and 4-sec-butylcycloheptyl, 2-, 3- and 4-tert-butylcycloheptyl, 2-, 3-, 4- and 5-methylcyclooctyl, 2-, 3-, 4- and 5-ethylcyclooctyl, 2-, 3-, 4- and 5-propylcyclooctyl.

Specific examples of substituted and unsubstituted cycloalkyl groups are cyclopropyl, cyclobutyl, cyclopentyl, 2- and 3-methylcyclopentyl, 2- and 3-ethylcyclopentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, cycloheptyl, 2-, 3- and 4-methyl-cycloheptyl, 2-, 3- and 4-ethylcycloheptyl, 3- and 4-propylcycloheptyl, 3- and 4-iso-propylcycloheptyl, 3- and 4-butylcycloheptyl, 3- and 4-sec-butylcycloheptyl, 3- and 4-tert-butylcycloheptyl, cyclooctyl, 2-, 3-, 4- and 5-methylcyclooctyl, 2-, 3-, 4- and 5-ethylcyclooctyl and 3-, 4- and 5-propylcyclooctyl; 3- and 4-hydroxycyclohexyl, 3- and 4-nitrocyclohexyl and 3- and 4-chlorocyclohexyl;

In the context of the present invention, aryl comprises mono- or polycyclic aromatic hydrocarbon radicals and monocyclic aromatic hydrocarbon radicals which may be fused to one or more unfused or fused saturated or unsaturated carbocyclic or heterocyclic five or six membered rings. Aryl has preferably 6 to 14, more preferably 6 to 10, carbon atoms. Examples of aryl are especially phenyl, naphthyl, indenyl, fluorenyl, anthracenyl, phenanthrenyl, naphthacenyl, chrysenyl and pyrenyl, especially phenyl, naphthyl and fluorenyl.

Substituted aryls may, depending on the number and size of their ring systems, have one or more (e.g. 1, 2, 3, 4, 5 or more than 5) substituents. These are preferably each independently selected from alkyl, alkoxy, alkylamino, alkylthio, cycloalkyl, heterocycloalkyl, aryl, hetaryl, fluorine, chlorine, bromine, cyano and nitro. The alkyl, alkoxy, alkylamino, alkylthio, cycloalkyl, heterocycloalkyl, aryl and hetaryl substituents on the aryl may in turn be unsubstituted or substituted. Reference is made to the substituents mentioned above for these groups. The substituents on the aryl are preferably selected from alkyl, alkoxy, haloalkyl, haloalkoxy, aryl, fluorine, chlorine, bromine, cyano and nitro. Substituted aryl is more preferably substituted phenyl which generally bears 1, 2, 3, 4 or 5, preferably 1, 2 or 3, substituents.

Substituted aryl is preferably aryl substituted by at least one alkyl group ("alkaryl"). Alkaryl groups may, depending on the size of the aromatic ring system, have one or more (e.g. 1, 2, 3, 4, 5, 6, 7, 8, 9 or more than 9) alkyl substituents. The alkyl substituents may be unsubstituted or substituted. In this regard, reference is made to the above statements regarding unsubstituted and substituted alkyl. In a preferred embodiment, the alkaryl groups have exclusively unsubstituted alkyl substituents. Alkaryl is preferably phenyl which bears 1, 2, 3, 4 or 5, preferably 1, 2 or 3, more preferably 1 or 2, alkyl substituents.

Aryl which bears one or more radicals is, for example, 2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutyl-phenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert-butylphenyl, 2,4-, 2,5-, 3,5- and 2,6-di-tert-butylphenyl and 2,4,6-tri-tert-butylphenyl; 2-, 3- and 4-methoxyphenyl, 2,4-, 2,5-, 3,5- and 2,6-dimethoxyphenyl, 2,4,6-trimethoxyphenyl, 2-, 3- and 4-ethoxyphenyl, 2,4-, 2,5-, 3,5- and 2,6-diethoxy-phenyl, 2,4,6-triethoxyphenyl, 2-, 3- and 4-propoxyphenyl, 2,4-, 2,5-, 3,5- and 2,6-dipropoxyphenyl, 2-, 3- and 4-isopropoxyphenyl, 2,4-, 2,5-, 3,5- and 2,6-diisopropoxyphenyl and 2-, 3- and 4-butoxyphenyl; 2-, 3- and 4-cyanophenyl.

The above remarks regarding unsubstituted or substituted aryl also apply to unsubstituted or substituted aryloxy and unsubstituted or substituted arylthio. Examples of aryloxy are phenoxy and naphthyloxy.

In the context of the present invention, hetaryl comprises heteroaromatic, mono- or polycyclic groups and monocyclic groups which may be fused to one or more unfused or fused saturated or unsaturated carbocyclic or heterocyclic five or six membered rings. In addition to the ring carbon atoms, these have 1, 2, 3, 4 or more than 4 of the ring heteroatoms. The heteroatoms are preferably selected from oxygen, nitrogen, selenium and sulfur. The hetaryl groups have preferably 5 to 18, e.g. 5, 6, 8, 9, 10, 11, 12, 13 or 14, ring atoms.

Monocyclic hetaryl groups are preferably 5- or 6-membered hetaryl groups, such as 2-furyl (furan-2-yl), 3-furyl (furan-3-yl), 2-thienyl (thiophen-2-yl), 3-thienyl (thiophen-3-yl), selenophen-2-yl, selenophen-3-yl, 1H-pyrrol-2-yl, 1H-pyrrol-3-yl, pyrrol-1-yl, imidazol-2-yl, imidazol-1-yl, imidazol-4-yl, pyrazol-1-yl, pyrazol-3-yl, pyrazol-4-yl, pyrazol-5-yl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 4H[1,2,4]-triazol-3-yl, 1,3,4-triazol-2-yl, 1,2,3-triazol-1-yl, 1,2,4-triazol-1-yl, pyridin-2-yl, pyridin-3-yl, pyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

Polycyclic hetaryl has 2, 3, 4 or more than 4 fused rings. The fused-on rings may be aromatic, saturated or partly unsaturated. Examples of polycyclic hetaryl groups are quinolinyl, isoquinolinyl, indolyl, isoindolyl, indolizinyl, benzofuranyl, isobenzofuranyl, benzothiophenyl, benzoxazolyl, benzisoxazolyl, benzthiazolyl, benzoxadiazolyl; benzothiadiazolyl, benzoxazinyl, benzopyrazolyl, benzimidazolyl, benzotriazolyl, benzotriazinyl, benzoselenophenyl, thienothiophenyl, thienopyrimidyl, thiazolothiazolyl, dibenzopyrrolyl (carbazolyl), dibenzofuranyl, dibenzothiophenyl, naphtho[2,3-b]-thiophenyl, naphtha[2,3-b]furyl, dihydroindolyl, dihydroindolizinyl, dihydroisoindolyl, dihydroquinolinyl, dihydroisoquinolinyl.

Substituted heteroaryls may, depending on the number and size of their ring systems, have one or more (e.g. 1, 2, 3, 4, 5 or more than 5) substituents. These are preferably each independently selected from alkyl, alkoxy, alkylamino, alkylthio, cycloalkyl, heterocycloalkyl, aryl, hetaryl, fluorine, chlorine, bromine, cyano and nitro. Halogen substituents are preferably fluorine, chlorine or bromine. The substituents are preferably selected from $C_1$-$C_6$-alkyl, $C_1$-$C_6$-alkoxy, hydroxyl, carboxyl, halogen and cyano.

The above remarks regarding unsubstituted or substituted heteroaryl also apply to unsubstituted or substituted heteroaryloxy and unsubstituted or substituted heteroarylthio.

Halogen represents fluorine, chlorine, bromine or iodine, preferably chlorine and bromine.

Alkali cation represents sodium, potassium, rubidium and cesium, preferably sodium and potassium.

R' in the tetraalkyl ammonium cation $[NR']^{4+}$ typically refers to methyl or tert.-butyl.

Further details on the preparation of the compounds according to the instant invention can be taken from the experimental section.

DSCs generally comprise the following elements: an electrically conductive layer (being part of or forming the working electrode or anode), a photosensitive layer generally comprising a semi-conductive metal oxide and a photosensitive dye, a charge transfer layer and another electrically conductive layer (being part of or forming the counter electrode or cathode).

Regarding further details of the construction of DSCs particular reference is made to WO 2012/001628 A1, which is hereby fully incorporated by reference.

EXPERIMENTAL PART

A1) Preparation of Compounds According to the Invention

General procedures for the preparation are given below (if not stated otherwise the variables have the meaning as defined in general formula I and II):

Procedure 1:

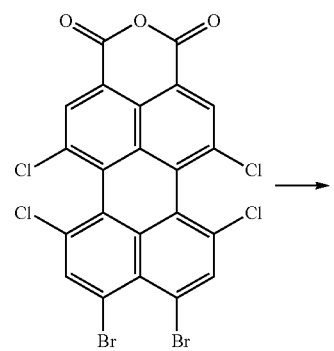

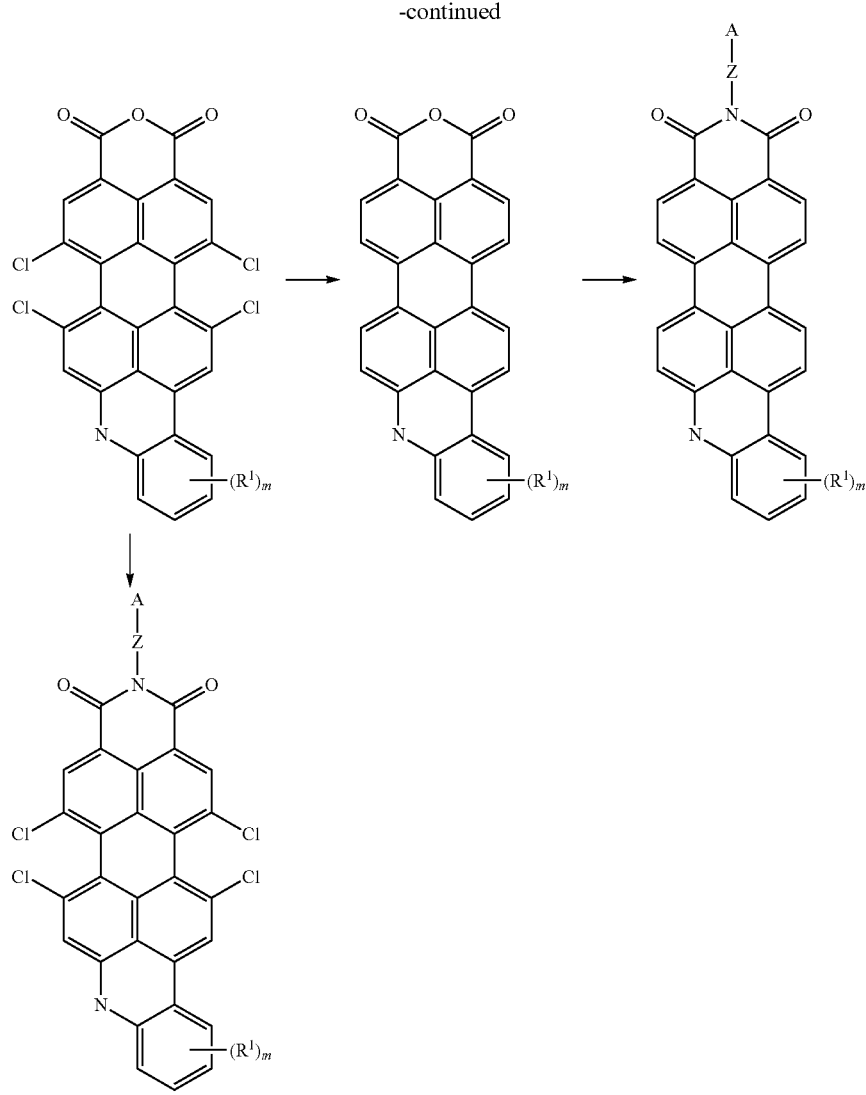
Procedure 2
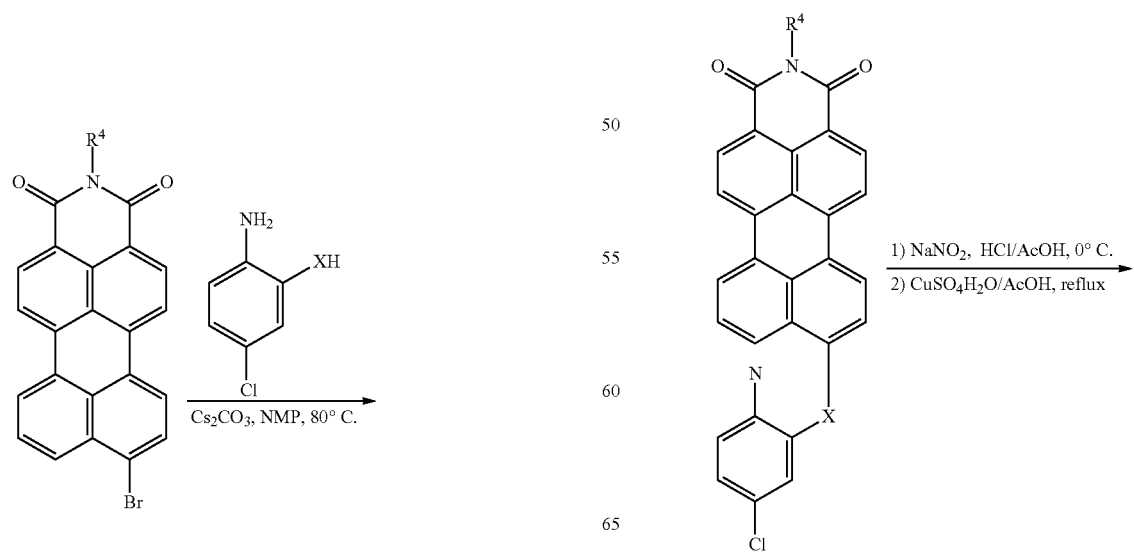

21
-continued
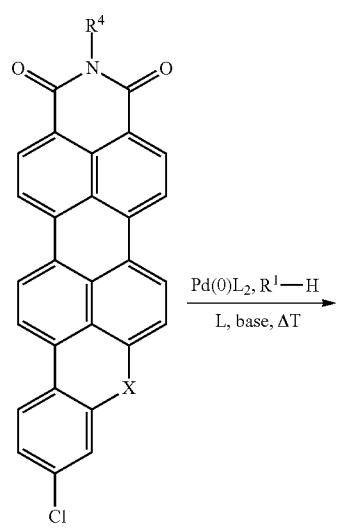
22
-continued
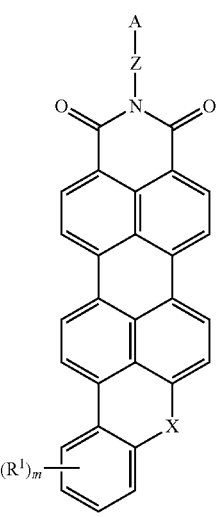
X = O, S
Procedure 3
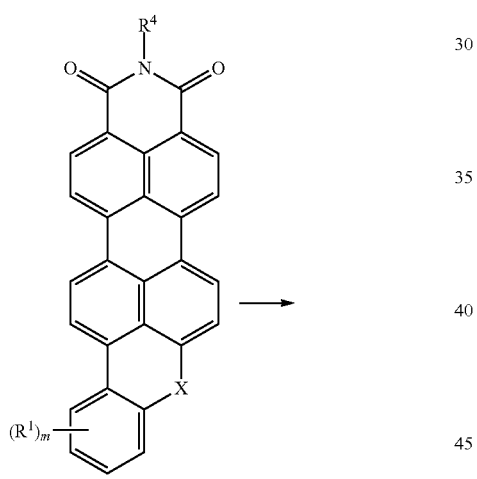
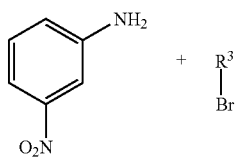
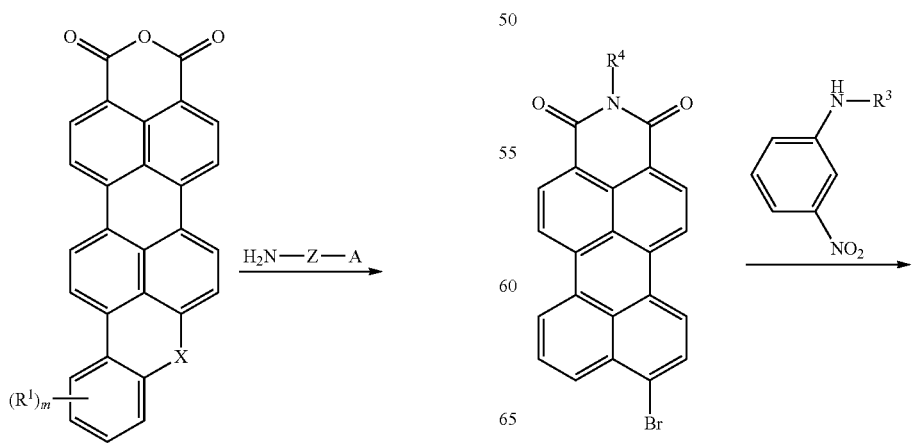

23
-continued

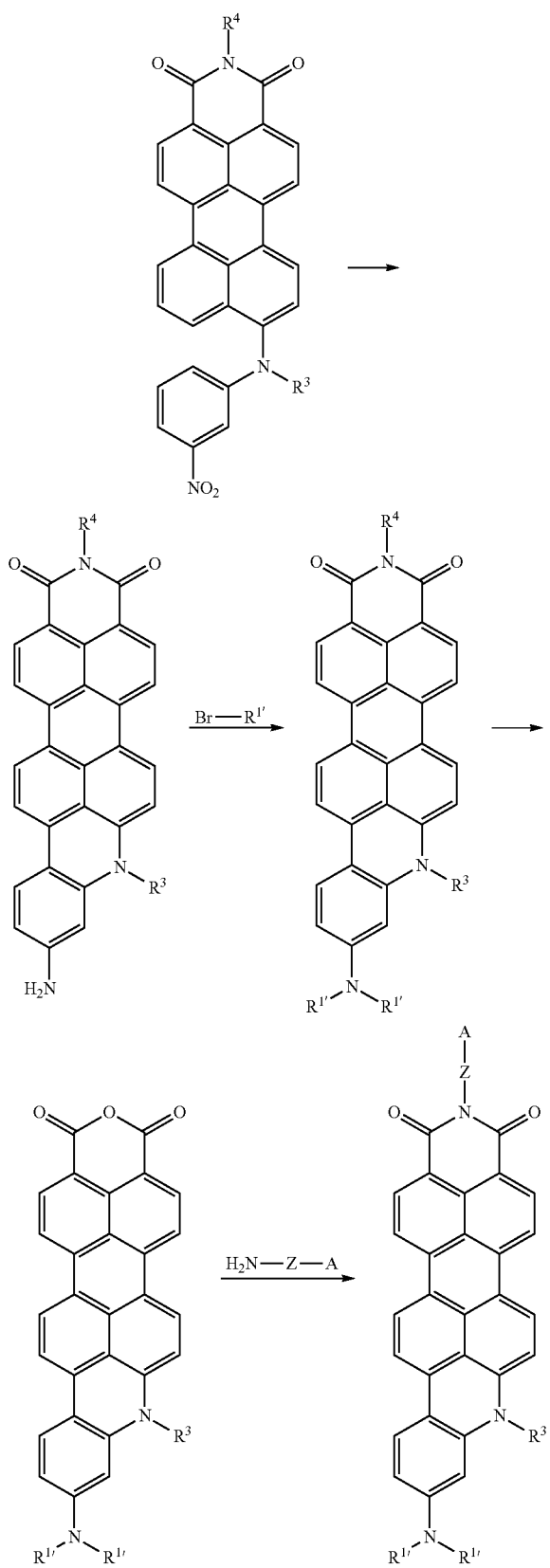

($R^{1'}$)$_2$N corresponds to definition of diarylamino of variable $R^1$ of general formula I

24

Preparation of compound 1: 5,6,14,15-tetrachloro-8-phenyl-1H-isochromeno-[6',5',4':10,5,6]anthra[2,1,9-mna]acridine-1,3(8H)-dione

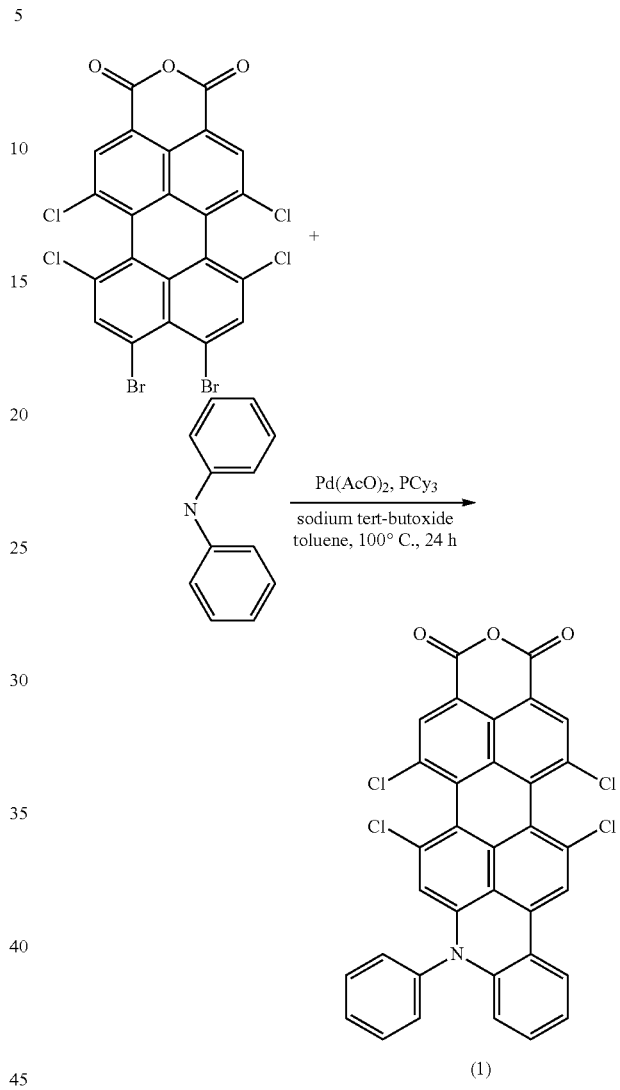

A suspension of 9,10-dibromo-1,6,7,12-tetrachloroperylene-3,4-dicarboxylic acid anhidride (1.24 g, 2.0 mmol), diphenylamine (0.40 g, 2.40 mmol), Pd(AcO)$_2$ (10 mmol %), sodium-tert-butoxide (0.48 g, 5.0 mmol), tricyclohexylphosphine (20 mol %) in 70 ml toluene was stirred at 100° C. under argon atmosphere for 24 h. The solvent was removed under reduced pressure. The solid was dissolved in dichloromethane and acetic acid and stirred overnight at 70° C. The solvent was removed under reduced pressure. The crude product was purified by column chromatography using dichloromethane as eluent on silica. Yield 0.50 g (40%).

$^1$H NMR (300 MHz, C$_2$D$_2$Cl$_4$, 300K): 6.49 (s, 1H); 6.71 (d, 1H, $^3J_{HH}$=8.3 Hz); 7.37-7.51 (m, 4H); 7.74-7.88 (m, 3H); 8.17 (s, 1H); 8.30 (d, 1H, $^3J_{HH}$=7.7 Hz); 8.50 (s, 1H); 8.55 (s, 1H).

FD mass spectrum (8 kV): m/z (%): calcd for 625.28. found: 623.6 (100) [M]$^+$UV-Vis (CH$_2$Cl$_2$): λ$_{max}$=693 (60 264) nm (M$^{-1}$cm$^{-1}$).

Preparation of compound 2: 2-(5,6,14,15-tetra-chloro-1,3-dioxo-8-phenylisoquinolino-[6',5',4':10,5,6]anthra[2,1,9-mna]acridin-2(1H,3H,8H)-yl)acetic acid

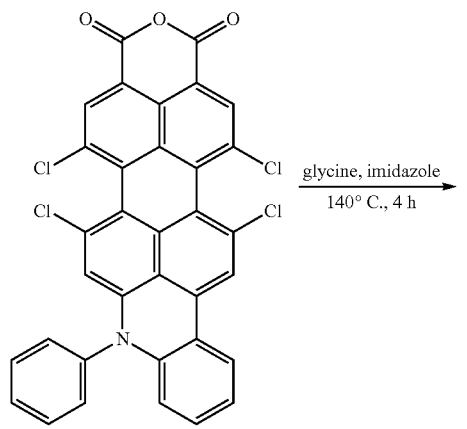

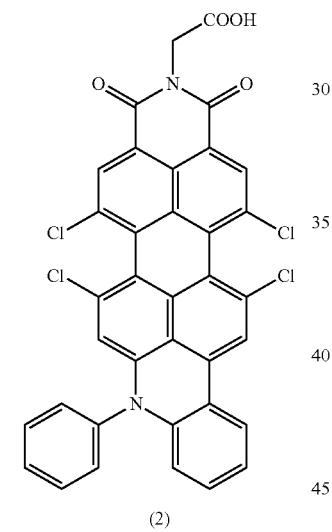

(2)

A mixture of Compound 1 (0.20 g, 0.32 mmol), glycine (0.20 g) and imidazole (2.0 g) was stirred at 140° C. under argon atmosphere for 4 h. The mixture was poured into 10% hydrochloric acid and ice. The precipitate was filtered, washed with water and water/methanol 1:1. The crude product was dissolved in THF and precipitated in water/methanol 1:2. Yield 0.20 g (92%).

$^1$H NMR (300 MHz, THF-d$_8$, 300K): 4.87 (s, 2H, CH$_2$COOH); 6.40 (s, 1H); 6.68 (d, 1H, $^3J_{HH}$=8.3 Hz); 7.31-7.43 (m, 2H); 7.53 (d, 1H, $^3J_{HH}$=7.7 Hz); 7.59 (d, 1H, $^3J_{HH}$=7.6 Hz); 7.73-7.89 (m, 3H); 8.33 (s, 1H); 8.46 (s, 1H); 8.47 (d, 1H, $^3J_{HH}$=7.3 Hz); 8.52 (s, 1H).

FD mass spectrum (8 kV): m/z (%): calcd for 682.34; found: 682.8 (100) [M]$^+$ UV-Vis (CH$_2$Cl$_2$): $\lambda_{max}$=681 (51 554) nm (M$^{-1}$cm$^{-1}$).

Preparation of compound 3: 5,6,14,15-tetrachloro-11-(2,4,4-trimethylpentan-2-yl)-8-(4-(2,4,4-trimethylpentan-2-yl)phenyl)-1H-isochromeno[6',5',4':10,5,6]anthra[2,1,9-mna]acridine-1,3(8H)-dione

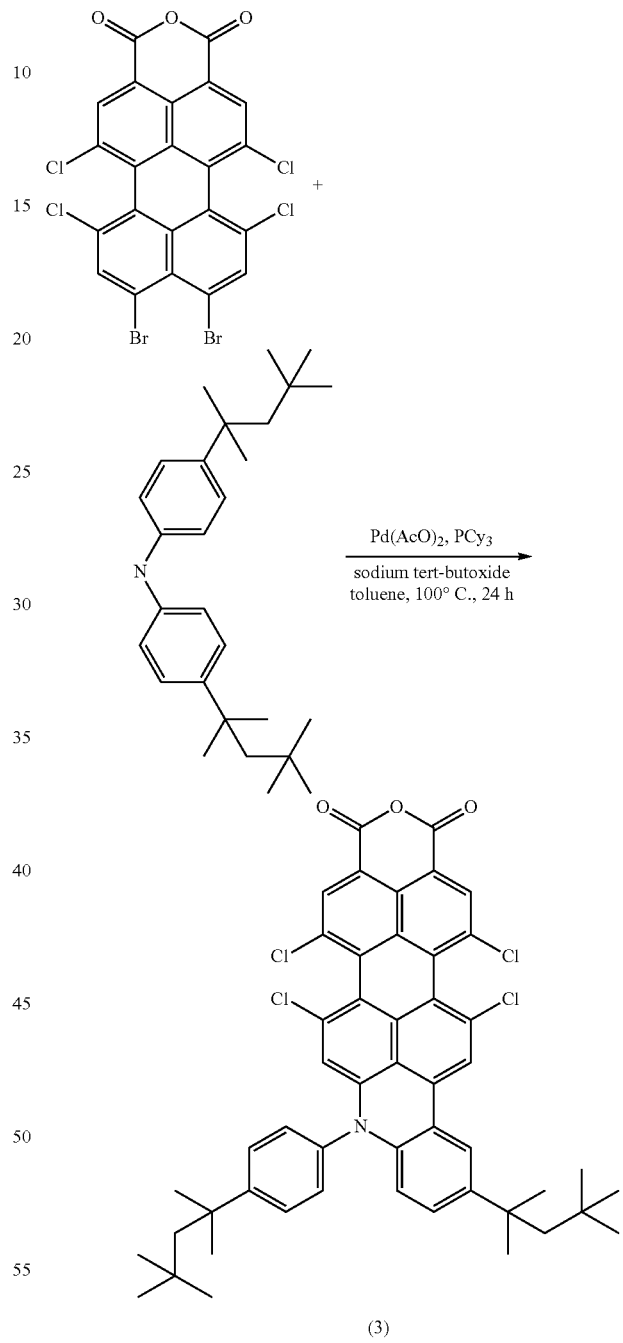

(3)

A suspension of 9,10-dibromo-1,6,7,12-tetrachloroperylene-3,4-dicarboxylic acid anhidride (0.62 g, 1.0 mmol), diphenylamine (0.47 g, 1.20 mmol), Pd(OAc)$_2$ (10 mmol %), sodium-tert-butoxide (0.24 g, 2.5 mmol), tricyclohexylphosphine (20 mol %) in 60 ml toluene was stirred at 100° C. under argon atmosphere for 24 h. The solvent was removed under reduced pressure. The solid was dissolved in dichloromethane and acetic acid and stirred overnight at 70°

C. The solvent was removed under reduced pressure. The crude product was purified by column chromatography using dichloromethane as eluent on silica. Yield 0.32 g (38%).

$^1$H NMR (300 MHz, $C_2D_2C_{14}$, 300K): 0.79 (s, 9H, $CH_3$); 0.87 (s, 9H, $CH_3$); 1.51 (s, 6H, $CH_3$); 1.54 (s, 6H, $CH_3$); 1.85 (s, 2H, $CH_2$); 1.89 (s, 2H, $CH_2$); 6.52 (s, 1H); 6.75 (d, 1H, $^3J_{HH}$=8.9 Hz); 7.33 (dd, 1H, $^3J_{HH}$=8.2 Hz, $^4J_{HH}$=2.1 Hz); 7.40 (dd, 1H, $^3J_{HH}$=8.3 Hz, $^4J_{HH}$=2.1 Hz); 7.53 (d, 1H, $^3J_{HH}$=8.7 Hz); 7.78-7.84 (m, 2H); 8.21 (s, 1H); 8.25 (d, 1H, $^4J_{HH}$=2.0 Hz); 8.51 (s, 1H); 8.55 (s, 1H).

FD mass spectrum (8 kV): m/z (%): calcd for 849.71. found: 850.4 (100) [M]$^+$ UV-Vis ($CH_2Cl_2$): $\lambda_{max}$=709 (64 776) nm ($M^{-1}cm^{-1}$).

Preparation of compound 4: 11-(2,4,4-trimethylpentan-2-yl)-8-(4-(2,4,4-trimethylpentan-2-yl)phenyl)-1H-isochromeno[6',5',4':10,5,6]anthra[2,1,9-mna]acridine-1,3(8H)-dione

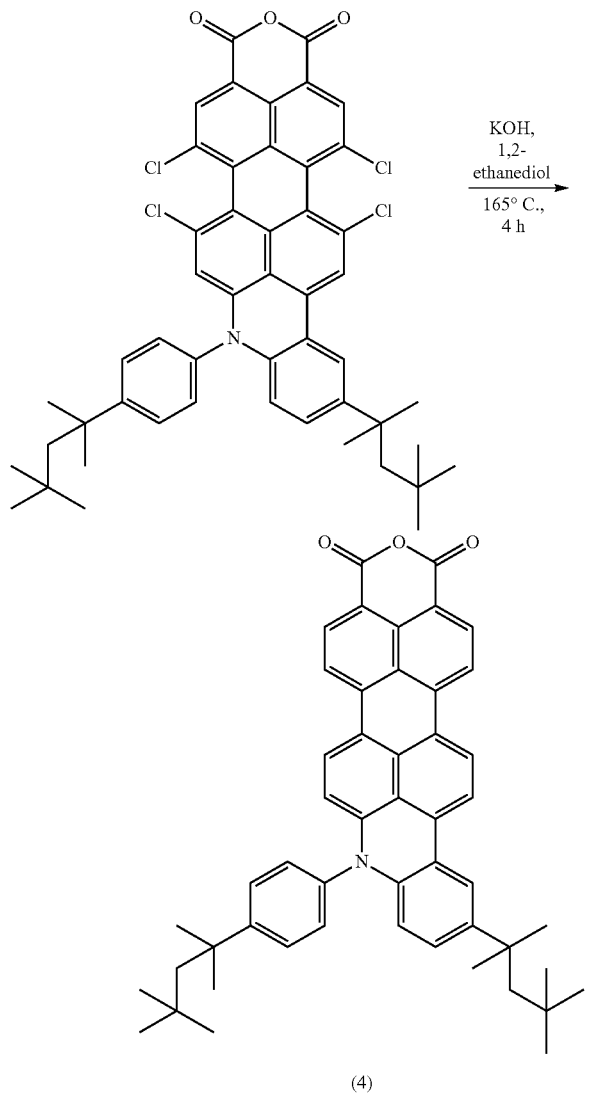

(4)

A mixture of potassium hydroxide (1.0 g) and Compound 3 (0.30 g, 0.35 mmol) in 10 ml 1,2-ethanediol was stirred an heated at 165° C. for 4 h. The mixture was cooled and diluted with 50 ml 10% hydrochloric acid. The precipitate was filtered, washed with water and dried. The solid was suspended in THF (20 ml) and acetic acid (20 ml) and stirred overnight at 100° C. The mixture was cooling down to room temperature and 10 ml of water was added. The precipitate was filtered, washed with water/methanol 1:2 and dried Yield 0.18 g (71%).

FD mass spectrum (8 kV): m/z (%): calcd for 711.93. found: 712.5 (100) [M]$^+$.

Preparation of compound 5: 2-(1,3-dioxo-11-(2,4,4-trimethylpentan-2-yl)-8-(4-(2,4,4-trimethylpentan-2-yl)phenypisoquinolino[6',5',4':10,5,6]anthra[2,1,9-mna]acridin-2(1H,3H,8H)-yl)acetic acid

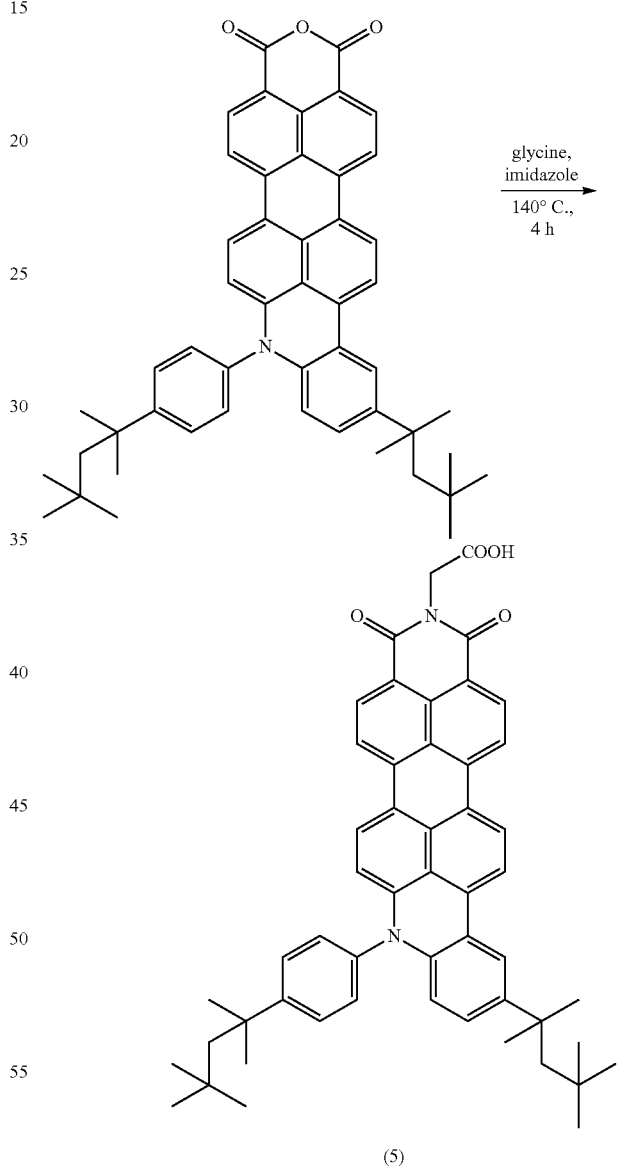

(5)

A mixture of Compound 4 (0.18 g, 0.25 mmol), glycine (0.20 g) and imidazole (2.0 g) was stirred at 140° C. under argon atmosphere for 4 h. The mixture was poured into 10% hydrochloric acid and ice. The precipitate was filtered, washed with water and water/methanol 1:1. The crude product was dissolved in THF and precipitated in water/methanol 1:2. The solid was dissolved in THF and purified by GPC using THF as eluent. Yield 0.14 g (73%).

$^1$H NMR (500 MHz, DMSO-d$_6$, 300K): 0.84 (s, 9H, CH$_3$); 0.91 (s, 9H, CH$_3$); 1.51 (s, 6H, CH$_3$); 1.54 (s, 6H, CH$_3$); 1.88 (s, 2H, CH$_2$); 1.93 (s, 2H, CH$_2$); 4.71 (s, 2H, CH$_2$); 6.34 (d, 1H, $^3J_{HH}$=8.8 Hz); 6.58 (d, 1H, $^3J_{HH}$=8.9 Hz); 7.44 (d, 2H, $^3J_{HH}$=8.3 Hz); 7.49 (d, 1H, $^3J_{HH}$=8.8 Hz); 7.85 (d, 2H, $^3J_{HH}$=8.4 Hz); 8.17 (d, 1H, $^3J_{HH}$=8.3 Hz); 8.28-8.31 (m, 2H); 8.35-8.39 (m, 3H); 8.43 (d, 1H, $^3J_{HH}$=8.9 Hz); 8.75 (d, 1H, $^3J_{HH}$=8.4 Hz).

FD mass spectrum (8 kV): m/z (%): calcd for 768.98. found: 768.2 (100) [M]$^+$.

UV-Vis (CH$_2$Cl$_2$): $\lambda_{max}$=730 (66 965) and 672 (46 837) nm (M$^{-1}$ cm$^{-1}$).

Preparation of compound 6: 9-(2,4,4-trimethylpentan-2-yl)-6-(4-(2,4,4-trimethylpentan-2-yl)phenyl)-1H-isochromeno[6,5,4-mna]acridine-1,3(6H)-dione

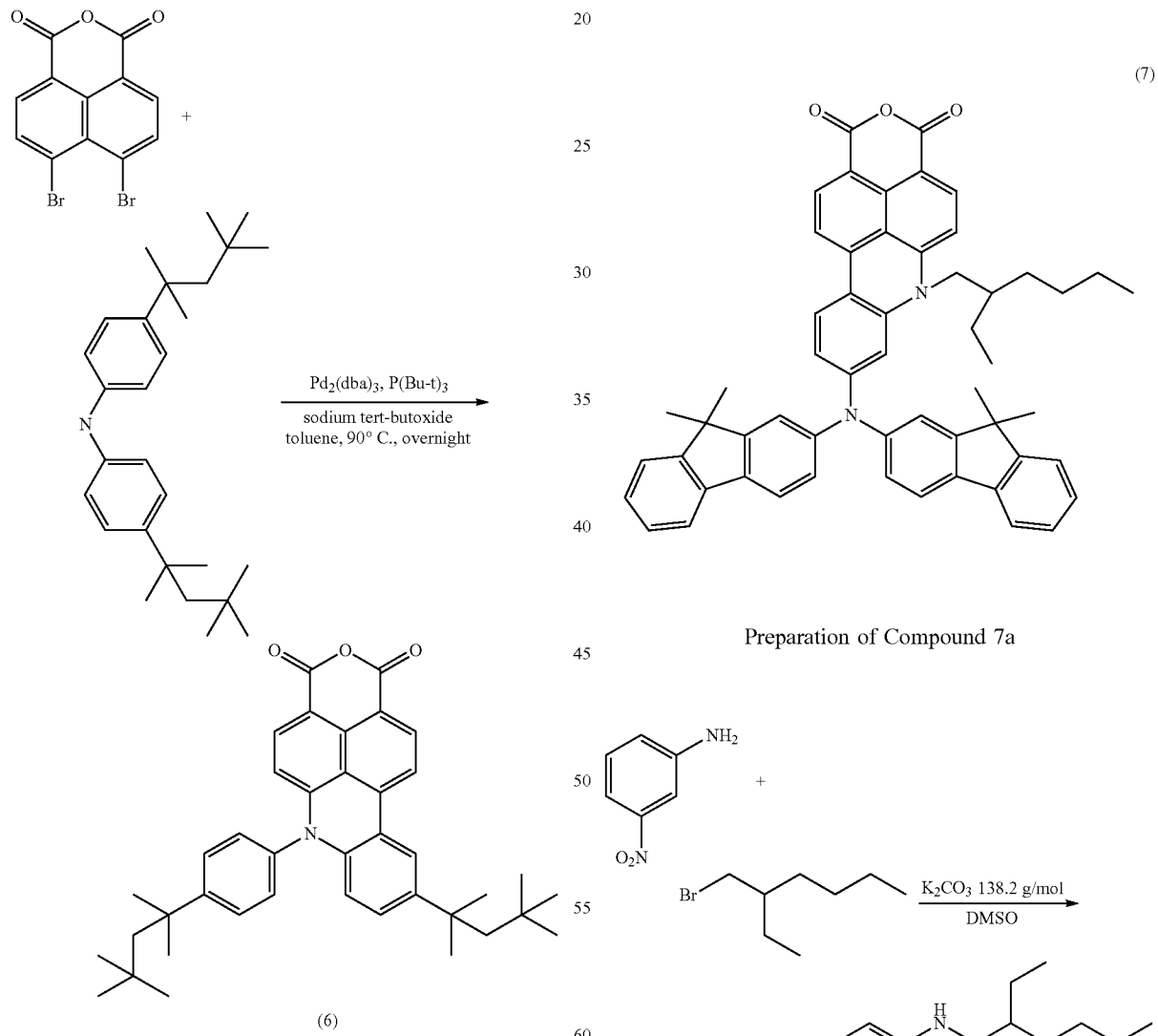

(6)

A mixture of 4,5-dibromo-1,8-naphthylanhydride (2.00 mmol), bis(4-(2,4,4-trimethylpentan-2-yl)phenyl)amine (3.0 mmol), Pd$_2$(dba)$_3$ (5 mmol %), sodium-tert-butoxide (3.0 mmol), tri(tert-butyl)phosphine (10 mol %) in 50 ml toluene was stirred at 90° C. under argon atmosphere overnight. The solvent was removed under reduced pressure. The solid was dissolved in dichloromethane and mixture of acetic acid and acetic anhydride and stirred overnight at room temperature. The solvent was removed under reduced pressure. The crude product was purified by column chromatography using hexane/dichloromethane as eluent on silica. Yield 0.30 g (25%).

FD-Mass: calc.: 587.79 found: 589.0.

$^1$H-NMR (δ (ppm), CDCl$_3$): 0.69 (s, 9H, CH$_3$); 0.77 (s, 9H, CH$_3$); 1.39 (s, 6H, CH$_3$); 1.44 (s, 6H, CH$_3$); 1.74 (s, 2H, CH$_2$); 1.81 (s, 2H, CH$_2$); 6.14 (d, 1H, $^3J_{HH}$=8.8 Hz); 6.54 (d, 1H, $^3J_{HH}$=9.0 Hz); 7.21 (d, 2H, $^3J_{HH}$=8.4 Hz); 7.35 (dd, 1H, $^3J_{HH}$=8.8 Hz, $^4J_{HH}$=1.9 Hz); 7.70 (d, 2H, $^3J_{HH}$=8.5 Hz); 7.88 (d, 1H, $^3J_{HH}$=8.3 Hz); 8.09 (d, 1H, $^3J_{HH}$=8.8 Hz); 8.12 (d, 1H, $^4J_{HH}$=1.8 Hz); 8.43 (d, 1H, $^3J_{HH}$=8.2 Hz).

UV-Vis (CH$_2$Cl$_2$): $\lambda_{max}$=512 (38 794) and 481 (30 399) nm (M$^{-1}$cm$^{-1}$).

Preparation of Compound 7

(7)

Preparation of Compound 7a (7a)

35.7 g of 3-nitroaniline (259 mmol), 100 g 2-ethylhexyl-bromide (518 mmol) and 71.5 g (518 mmol) potassium carbonate were added to 75 mL of DMSO and stirred at 110° C. for 3 days. The reaction mixture was poured into water and extracted with dichloromethane. The product was purified via column chromatography with n-hexane:DCM 2:1. Yield: 34.8 g (54%)

$^1$H-NMR (δ (ppm), CD$_2$Cl$_2$): 0.92 (m, 6H), 1.39 (m, 8H), 1.60 (m, 1H); 3.08 (t, 2H, $^3J_{HH}$=5.1 Hz), 4.09 (s, 1H, NH), 6.89 (m, 1H), 7.27 (t, 1H, $^3J_{HH}$=8.1 Hz), 7.37 (t, 1H, $^3J_{HH}$=2.3 Hz), 7.45 (m, 1H)

Preparation of Compound 7b

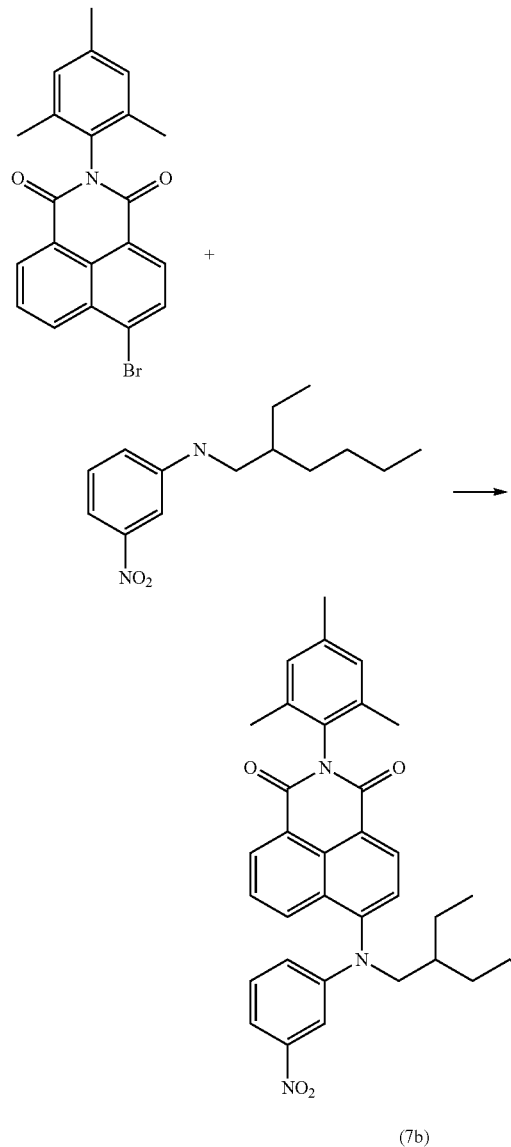

(7b)

9.9 g of 6-bromo-2-(2,4,6-trimethylphenyl)benzo[de]isoquinoline-1,3-dione (25 mmol), 1.2 g Pd$_2$(dba)$_3$ (5 mmol %), 3.6 g sodium-tert-butoxide (37.5 mmol), 5.1 g tri(tert-butyl) phosphine (37.5 mmol) were added to 50 mL toluene containing 9.4 g of N-(2-ethylhexyl)-3-nitro-aniline (37.5 mmol) and stirred under argon overnight at 90° C. The reaction mixture was cooled down to room temperature, the organic phase separated, and the rest of product extracted with dichloromethane. The solvent was removed under vacuum and purified under MPL chromatography. Yield: 7.2 g (51%)

$^1$H-NMR (δ (ppm), CD$_2$Cl$_2$): 0.81 (t, 3H, $^3J_{HH}$=6.8 Hz), 0.88 (t, 3H, $^3J_{HH}$=7.5 Hz), 1.23 (m, 4H), 1.41 (m, 4H), 1.83 (m, 1H), 2.09 (s, 6H), 2.38 (s, 3H), 3.92, (d, 2H, $^3J_{HH}$=7.0 Hz), 6.93 (d, 1H, $^3J_{HH}$=11.0 Hz), 7.06 (s, 2H), 7.29 (t, 1H, $^3J_{HH}$=8.2 Hz), 7.58 (s, 1H), 7.64 (dt, 2H, $^3J_{HH}$=7.6 Hz), 7.75 (d, 1H, $^3J_{HH}$=7.8 Hz), 8.10 (d, 1H, $^3J_{HH}$=8.6 Hz), 8.59 (d, 1H, $^3J_{HH}$=7.4 Hz), 8.70 (d, 1H, $^3J_{HH}$=7.8 Hz)

Preparation of Compound 7c

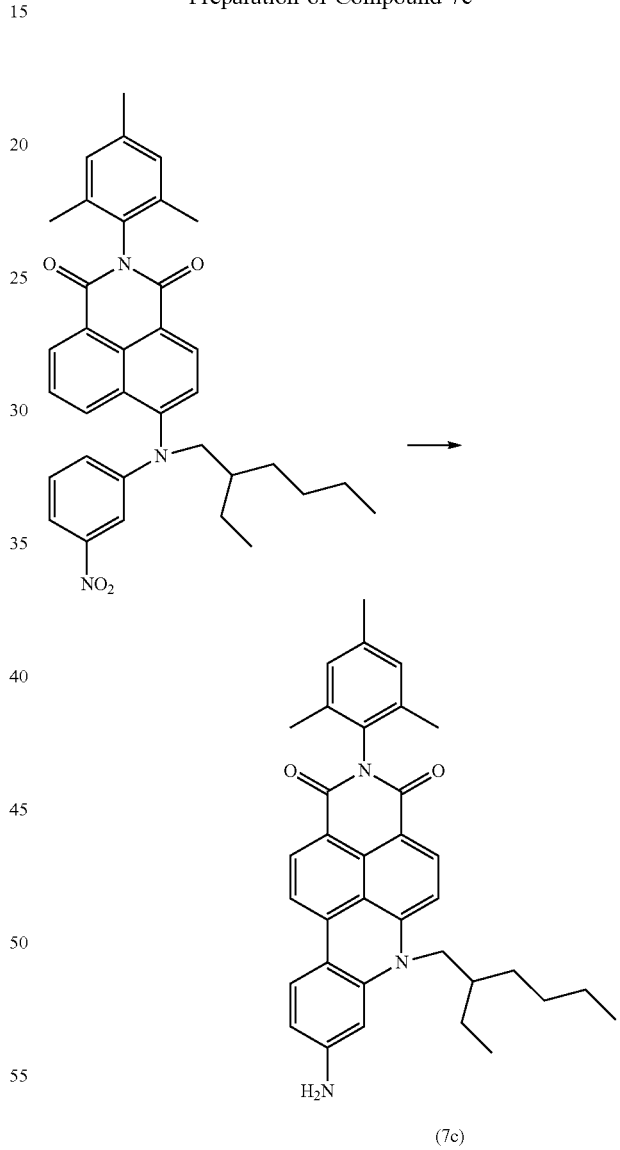

(7c)

5 g of 6-[N-(2-ethylhexyl)-3-nitro-anilino]-2-(2,4,6-trimethylphenyl)benzo[de]-isoquinoline-1,3-dione (8.9 mmol) and 14.8 g (107 mmol) potassium carbonate were added to 100 mL of ethanolamine and stirred for 3 days at 125° C. The reaction mixture was cooled down to room temperature followed by the addition of distilled water and acidified with acetic acid to pH 6. The precipitate was filtered, washed with hot water and dried under vacuum at 80° C. The dried material was purified by column chromatography with dichloromethane:methanol 19:1. Yield: 2.3 g (48%)

$^1$H-NMR (δ (ppm), CD$_2$Cl$_2$): 0.87 (t, 3H, $^3J_{HH}$=6.9 Hz), 0.95 (t, 3H, $^3J_{HH}$=7.4 Hz), 1.38 (m, 8H), 2.03 (s, 6H), 2.16 (s, 1H), 2.37 (s, 3H), 4.21 (d, 2H, $^3J_{HH}$=7.8 Hz), 4.27 (s, 2H), 6.71 (d, 2H, $^3J_{HH}$=10.3 Hz), 7.03 (s, 2H), 7.07 (d, 1H, $^3J_{HH}$=8.8 Hz), 7.84 (d, 1H, $^3J_{HH}$=8.2 Hz), 8.11 (d, 1H, $^3J_{HH}$=8.8 Hz), 8.50 (dd, 2H, $^3J_{HH}$=8.1 Hz, $^4J_{HH}$=11.5 Hz)

Preparation of Compound 7d

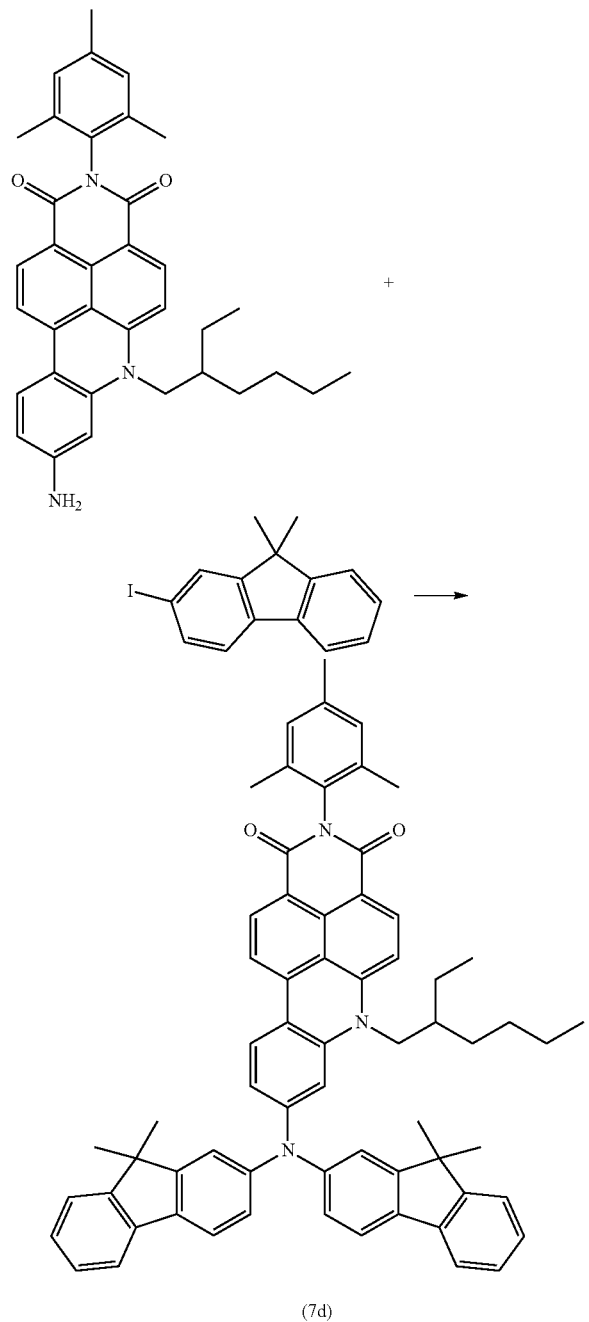

(7d)

2.3 g of compound 7c (4.3 mmol), 4.9 g 2-iodo-9,9-dimethyl-fluorene (12.9 mmol), 42 mg copper(I) iodide (5 mol %), 4.2 g cesium carbonate (12.9 mmol) were purged with argon and 40 mL of THF containing 93 mg of N,N'-dimethylethylenediamine (85% solution) was added and stirred for 3 days under reflux. The product was extracted with dichloromethane and purified by column chromatography with dichloromethane. Yield: 2.5 g (63%)

$^1$H-NMR (δ (ppm), CD$_2$Cl$_2$): 0.66 (m, 3H), 1.13 (m, 8H), 1.44 (s, 12H), 1.90 (m, 1H), 2.04 (s, 6H), 2.36 (s, 3H), 4.00 (s, 2H), 7.03 (s, 3H), 7.09 (s, 1H), 7.16 (d, 1H, $^3J_{HH}$=8.8 Hz), 7.23 (d, 2H, $^3J_{HH}$=8.2 Hz), 7.34 (m, 6H), 7.44 (d, 2H, $^3J_{HH}$=7.2 Hz), 7.7 (m, 4H), 7.90 (d, 1H, $^3J_{HH}$=8.4 Hz), 8.16 (d, 1H, $^3J_{HH}$=8.7 Hz), 8.46 (d, 1H, $^3J_{HH}$=8.8 Hz), 8.55 (d, 1H, $^3J_{HH}$=8.2 Hz)

Preparation of Target Compound 7

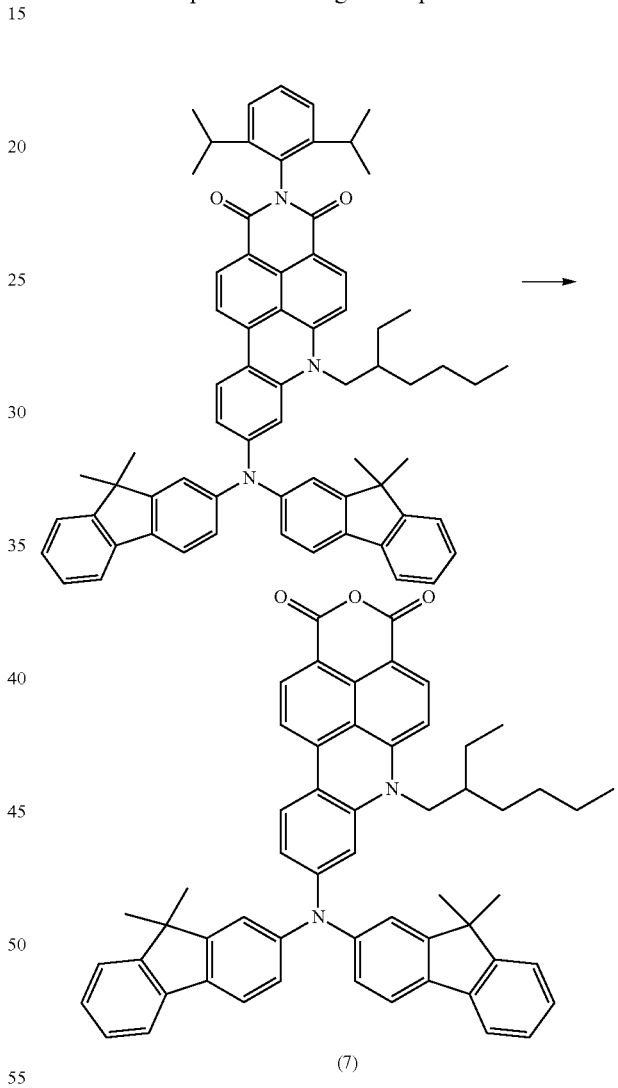

(7)

2.5 g of compound 7d (2.73 mmol) were dissolved in 50 mL 2-methyl-2-butanol, followed by the addition of 6.13 g of potassium hydroxide (109.2 mmol). The reaction mixture was refluxed under argon overnight and cooled down to room temperature.

The product was precipitated in ice water/acetic acid solution, filtered, washed with hot water, and dried under vacuum at 80° C. The solid was dissolved in dichloromethane, suspended in acetic acid for one hour, filtered, washed with a small portion of methanol and dried under vacuum at 70° C. Yield: 1.8 g (82%)

¹H-NMR (δ (ppm), CD₂Cl₂): 0.65 (m, 6H), 1.11 (m, 8H), 1.46 (s, 12H), 1.85 (m, 1H), 3.94 (s, 2H), 6.93 (d, 1H, $^3J_{HH}$=8.8 Hz), 7.05 (s, 1H), 7.16 (d, 2H, $^3J_{HH}$=9.3 Hz), 7.31 (m, 6H), 7.40 (s, 2H), 7.44 (d, 2H, $^3J_{HH}$=7.1 Hz), 7.71 (m, 5H), 8.03 (d, 1H, $^3J_{HH}$=9.0 Hz), 8.29 (m, 2H)

Preparation of Compound 8

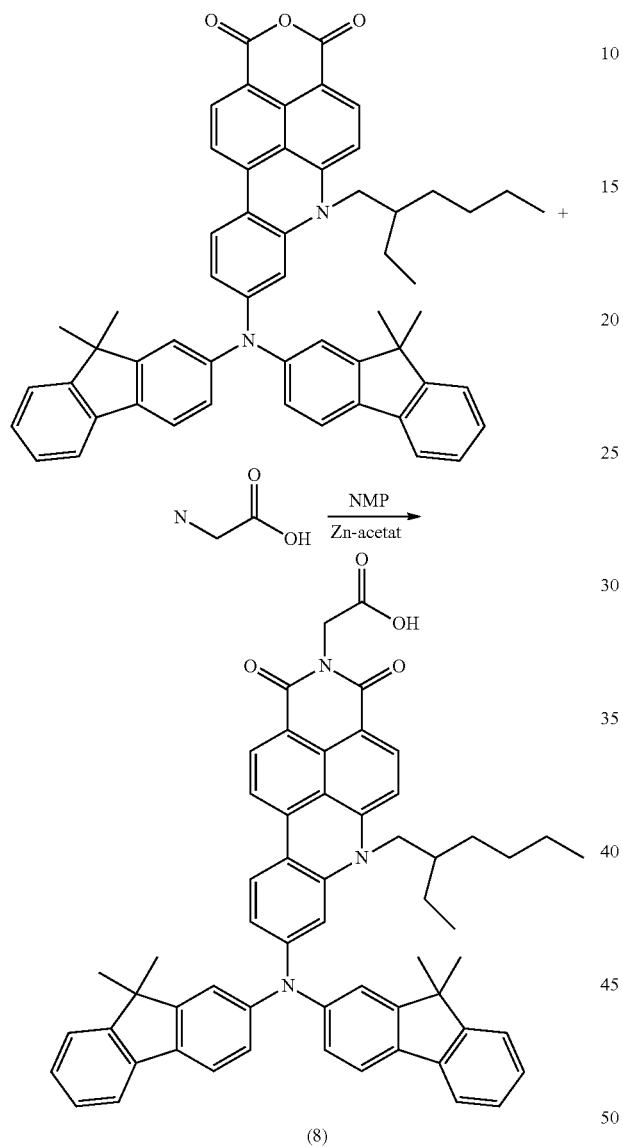

(8)

0.9 g of compound 7 (1.1 mmol), 207 mg zinc acetate (1.1 mmol), and 580 mg glycine (11.3 mmol) were added to 50 mL N-methylpirrolidone and stirred over night at 130° C. The reaction mixture was cooled down to room temperature and the product was precipitated from ice water. The mixture was acidified to pH 6 with acetic acid, the solid was filtered, washed with water and dried under vacuum at 80° C. The product was purified by column chromatography with the following gradients: 1-dichloromethane with 2% trietanolamine, dichloromethane: Methanol 19:1 with 2% triethylamine. The fractions containing product were combined and the solvent removed under vacuum. The resulting solid was stirred with acetic acid at 70° C., filtered, washed with hot water, methanol, and dried under vacuum at 70° C. Yield: 510 mg (53%)

¹H-NMR (δ (ppm), CD₂Cl₂): 0.62 (m, 6H), 1.08 (m, 8H), 1.44 (s, 12H), 1.88 (m, 1H), 3.98 (s, 2H), 4.93 (s, 2H), 7.03 (d, 1H), 7.09 (s, 1H), 7.16 (d, 1H, $^3J_{HH}$=8.4 Hz), 7.23 (dd, 2H, $^3J_{HH}$=1.5 Hz, $^4J_{HH}$=5.0 Hz), 7.33 (m, 6H), 7.44 (d, 2H, $^3J_{HH}$=5.7 Hz), 7.71 (m, 4H), 7.87 (d, 1H, $^3J_{HH}$=6.5 Hz), 8.15 (d, 1H, $^3J_{HH}$=7.3 Hz), 8.44 (d, 1H, $^3J_{HH}$=7.1 Hz), 8.53 (d, 1H, $^3J_{HH}$=6.6 Hz)

Preparation of Compound 9

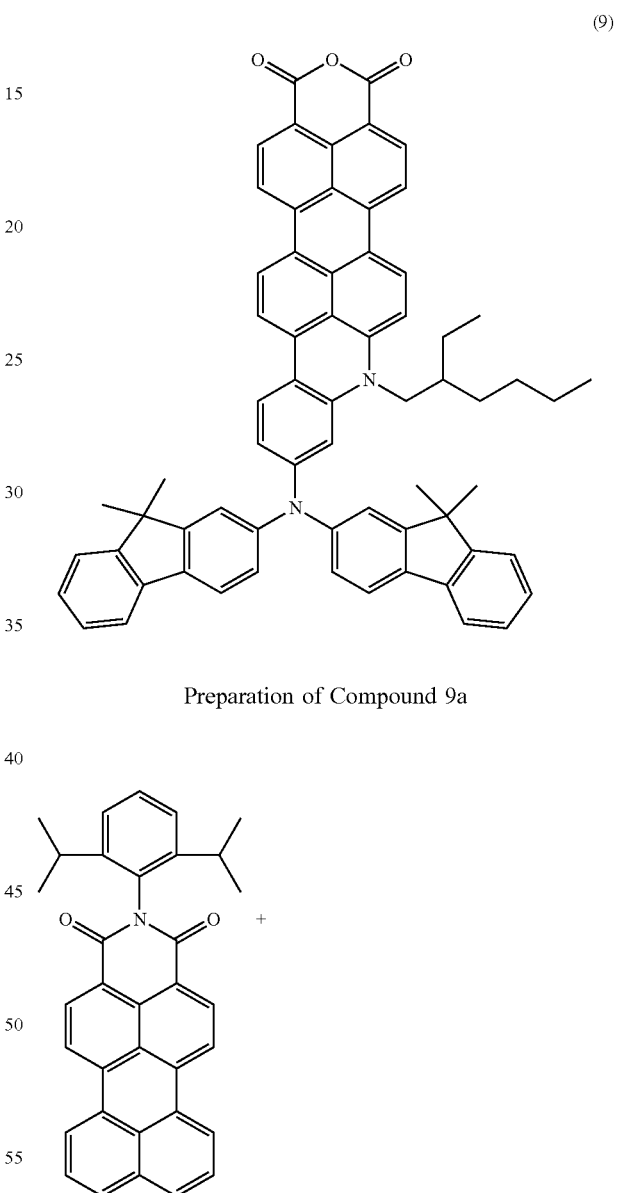

(9)

Preparation of Compound 9a

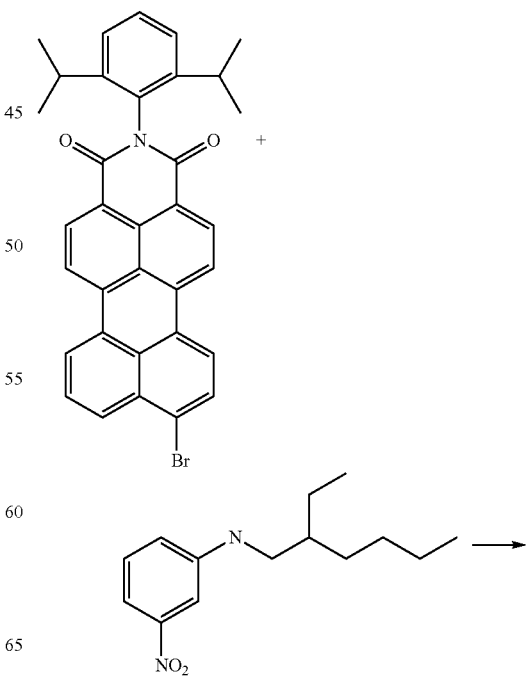

-continued

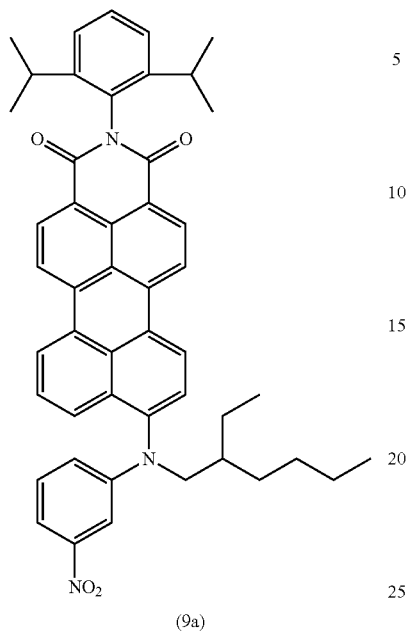

(9a)

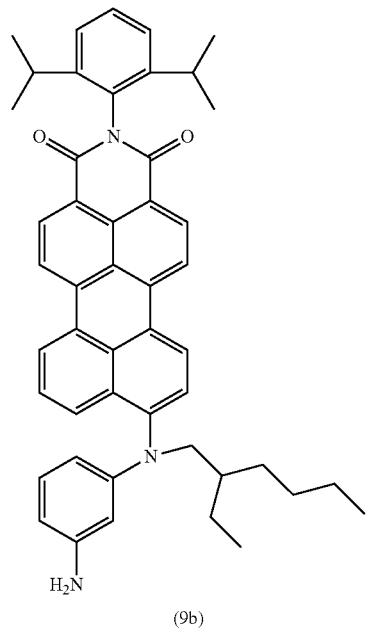

(9b)

6.00 g (24 mmol) of compound 7a and 9.00 g (16 mmol) of 9-Br-DIPP-PDC were dissolved in 100 mL of dry toluene. 733 mg of $Pd_2(dba)_3$ (0.8 mmol), 3.4 g of tris-(t-butyl) phosphine (10% in toluene) (1.6 mmol) and 2.3 g (24 mmol) of NaOtBu were added and stirred at 90° C. for 2 days.

The crude mixture was purified via column chromatography on silica with DCM:hexane 2:1. Yield: 3.7 g 2.2 g (3 mmol) of compound 8a and 5 g (36 mmol) of potassium carbonated were stirred in 100 mL of ethanol amine at 125° C. overnight. The reaction mixture was cooled down to room temperature and poured into water. Acetic acid was added until the pH 5. The precipitate was filtered, washed with hot water and dried.

MALDI-MS: calc.: 697.93 found: 697.35.

Preparation of Compound 9b

Preparation of Compound 9c

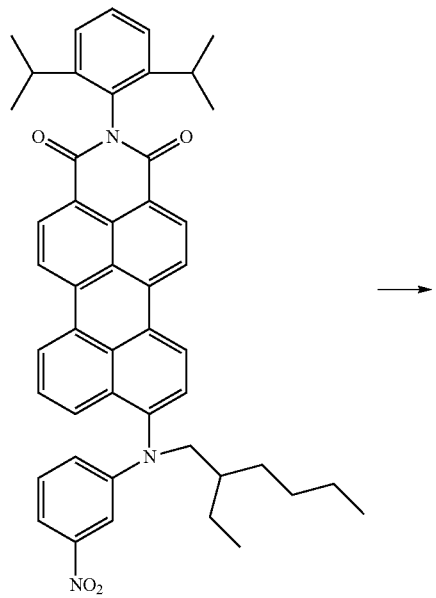

→

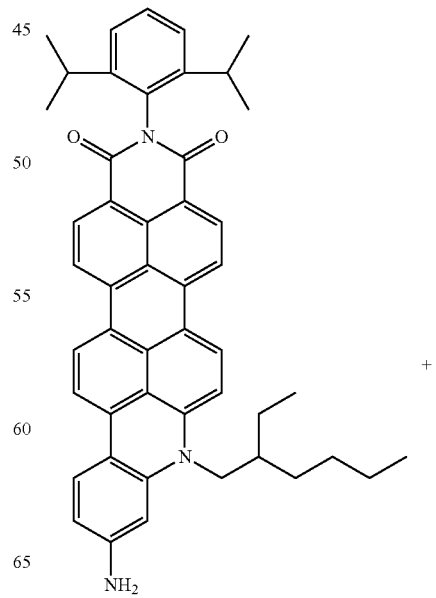

+

-continued

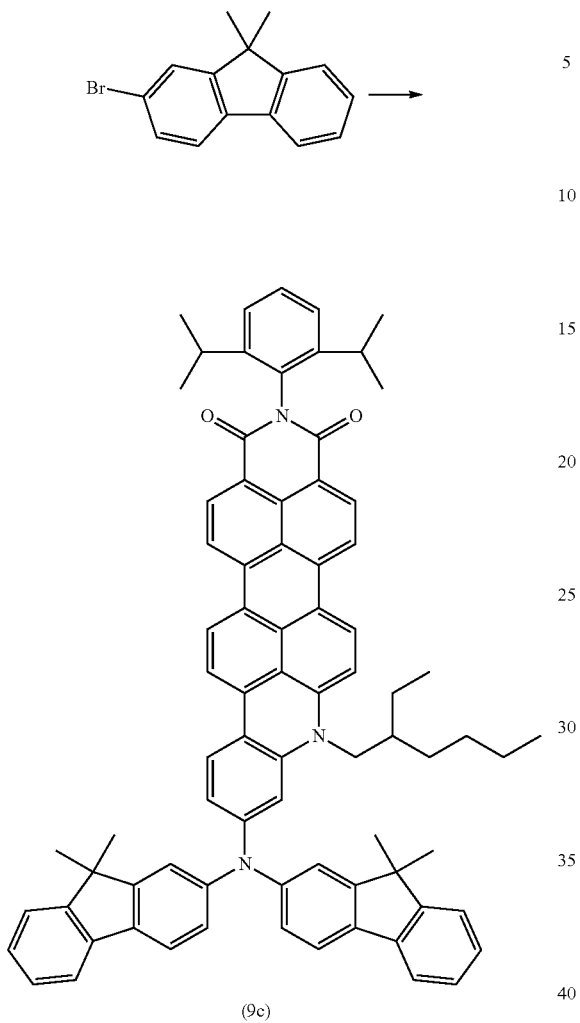

(9c)

Preparation of Target Compound 9

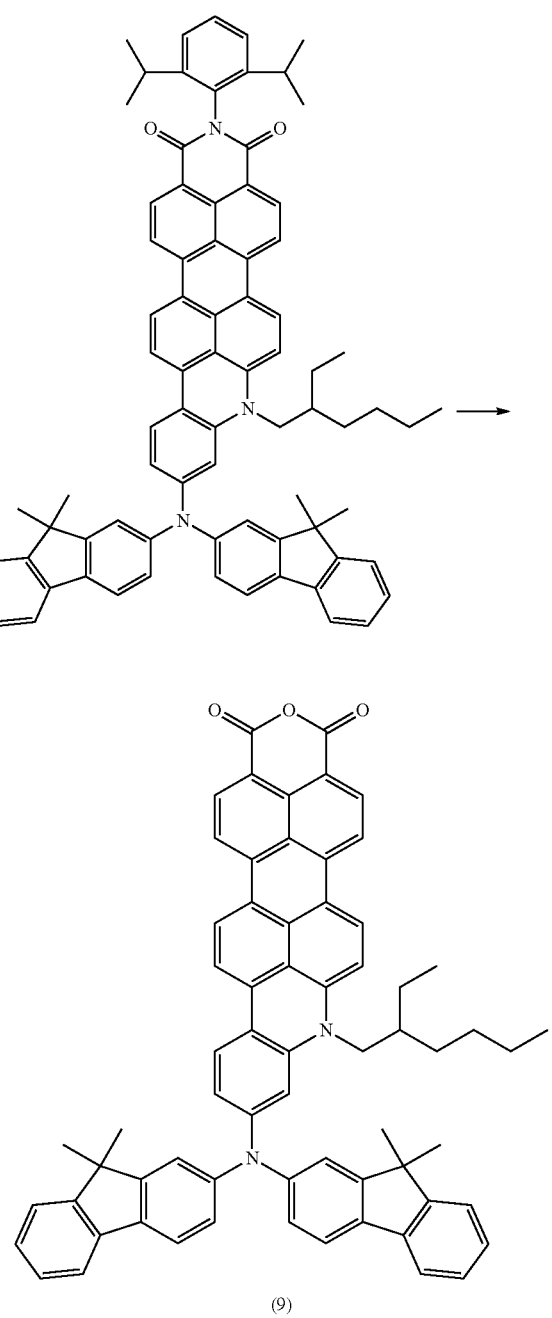

(9)

1.5 g (2.15 mmol) of compound 9b and 1.8 g of 2-bromo-9,9-dimethylfluorene (6.6 mmol), 270 mg (2.8 mmol) of NaOtBu, 275 mg of $Pd_2(dba)_3$ (0.3 mmol) and 1.9 g (0.9 mmol) of tri-(t-butyl)phosphine (10% in toluene) were stirred in 50 mL of dry toluenen at 80° C. overnight. The reaction mixture was cooled down to room temperature and 590 mg (2.15 mmol) 2-bromo-9,9-dimethylfluorene, 270 mg (2.8 mmol) NaOtBu, 275 mg (0.3 mmol) Pd2(dba)3 and 0.9 mg (1.9 mmol) tri-(t-butyl)phosphine (10% in toluene) were added and stirred at 80° C. for 2 more days. The reaction mixture was cooled down to room temperature and filtered over celite and washed and extracted with DCM. The crude product was purified via column chromatography on silica with DCM. Yield: 1.3 g (56%)

$^1$H-NMR (δ (ppm), $CD_2Cl_2$): 0.68 (m, 6H), 1.14 (d, 12H, $^3J_{HH}$=5.4 Hz), 1.24 (m, 8H), 1.45 (s, 12H), 1.93 (m, 1H), 2.74 (m, 2H), 4.00 (s, 2H), 7.13 (m, 4H), 7.25 (d, 2H, $^3J_{HH}$=6.1 Hz), 7.33 (m, 6H), 7.46 (m, 4H), 7.72 (m, 4H), 7.95 (d, 1H, $^3J_{HH}$=7.2 Hz), 8.15 (m, 2H), 8.26 (d, 1H, $^3J_{HH}$=7.4 Hz), 8.51 (m, 1H), 8.59 (d, 1H, $^3J_{HH}$=7.2 Hz)

1.3 g (1.2 mmol) of compound 9c were dissolved in 100 mL of 2-methyl-2-butanol. 2.7 g (48 mmol) of potassium hydroxide were added and refluxed overnight. The mixture was poured into a mixture of acetic acid and ice water. The precipitate was filtered, washed with water and dissolved in Methanol and Acetic acid (~100:1) for 1 h. The solvent was removed under reduced pressure and methanol added. The precipitate was filtered and dried. Yield: 1 g MALDI-MS: calc.: 922.41 found: 922.43.

Preparation of Compounds 10 and 11

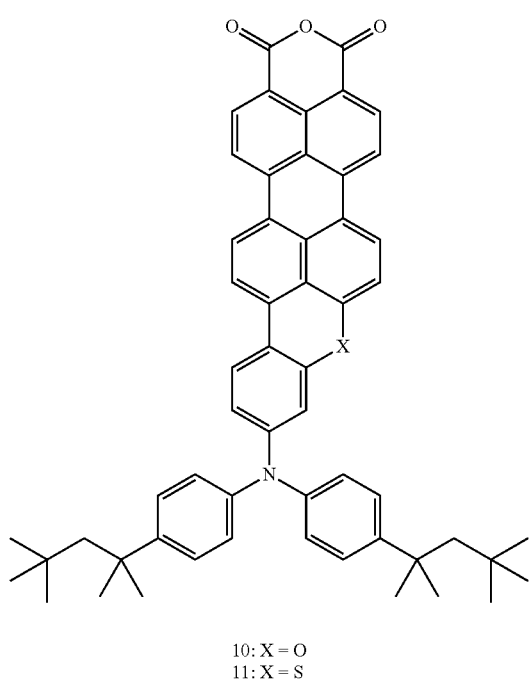

10: X = O
11: X = S

Preparation of Compound 10a and 11a

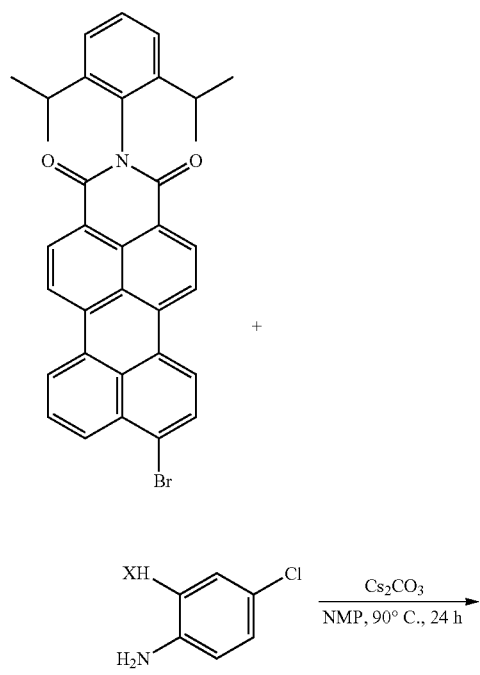

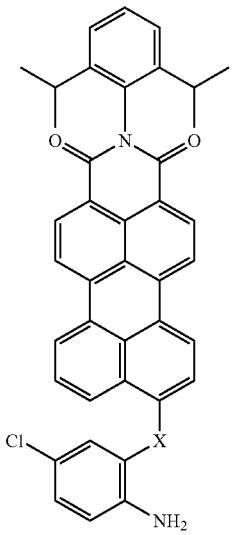

(10a/11a)
10a: X = O
11a: X = S

9-(2-amino-5-chlorophenoxy)-N-(2,6-diisopropylphenyl)-3,4-perylenedicarboxylic acid imide (compound 10a)

A mixture of 9-Bromo-N-(2,6-diisopropylphenyl)-3,4-perylenedicarboxylic acid imide (0.561 g, 1.0 mmol), 2-amino-5-chlorophenol (0.158 g, 1.1 mmol), cesium carbonate (0.390 g, 1.2 mmol) in 25 ml of NMP was stirred at 90° C. under argon atmosphere for 24 h. The crude product was precipitated by 50 ml 1M HCl solution, was filtrated and dried under reduced pressure. The crude product was purified by column chromatography using Toluene/EtOAc (5:1) mixture as eluent on silica. Yield: 51% (0.320 g, 0.51 mmol) of a dark red solid.

$^1$H NMR (250 MHz, CD$_2$Cl$_2$, 298K): 1.20 (d, 12H, $^3J_{HH}$=6.7 Hz), 0.2.83 (h, 2H $^3J_{HH}$=6.5 Hz), 4.14 (s, 2H), 6.93-6.80 (m, 3H), 7.04 (m, 1H), 7.34 (m, 2H), 7.52-7.32 (m, 2H), 8.03 (d, 1H, $^3J_{HH}$=8.2 Hz), 8.16 (m, 2H), 8.40 (d, 1H, $^3J_{HH}$=8.2 Hz), 8.51 (m, 2H).

FD mass spectrum (8 kV): m/z (%): calcd for 623.14. found: 623.6 (100), 621.7 (85) [M]$^+$ UV-Vis (CH$_2$Cl$_2$): $\lambda_{max}$=509 nm (43626 M$^{-1}$cm$^{-1}$).

9-(2-amino-5-chlorothiophenoxy)-N-(2,6-diisopropylphenyl)-3,4-perylenedicarboxylic acid imide (compound 11a)

A mixture of 9-Bromo-N-(2,6-diisopropylphenyl)-3,4-perylenedicarboxylic acid imide (0.561 g, 1.0 mmol, 2-amino-5-chlorothiophenol (0.176 g, 1.1 mmol), cesium carbonate (0.390 g, 1.2 mmol) in 25 ml of NMP was stirred at 90° C. under argon atmosphere for 24 h. The crude product was precipitated by 50 ml 1M HCl solution, was filtrated and dried under reduced pressure. The crude product was purified by column chromatography using Toluene/EtOAc (5:1) mixture as eluent on silica. Yield: 64% (0.410 g, 0.641 mmol) of a dark red solid.

$^1$H NMR (300 MHz, CD$_2$Cl$_2$, 298K): 1.15 (d, 12H, $^3J_{HH}$=6.7 Hz), 0.2.85-2.72 (h, 2H $^3J_{HH}$=6.8 Hz), 4.48 (s, 2H), 6.85 (d, 1H, $^3J_{HH}$=8.7 Hz), 7.04 (d, 1H, $^3J_{HH}$=8.1 Hz), 7.32 (m, 3H), 7.51 (m, 2H), 7.65 (t, 1H, $^3J_{HH}$=8.0 Hz), 8.22 (d, 1H, $^3J_{HH}$=8.3 Hz), 8.30 (d, 2H, $^3J_{HH}$=8.0 Hz), 8.40 (d, 1H, $^3J_{HH}$=8.2 Hz), 8.46 (d, 1H, $^3J_{HH}$=7.7 Hz), 8.57 (t, 2H, $^3J_{HH}$=8.5 Hz).

FD mass spectrum (8 kV): m/z (%): calcd for 639.20. found: 637.60 (100), 641.1 (74) [M]$^+$ UV-Vis (CH$_2$Cl$_2$): $\lambda_{max}$=516 nm (42364 M$^{-1}$cm$^{-1}$).

Preparation of Compound 10b and 11b

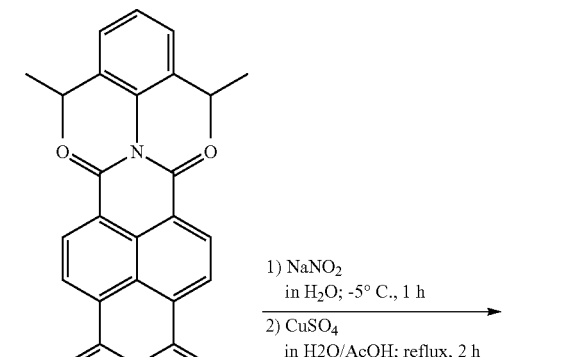

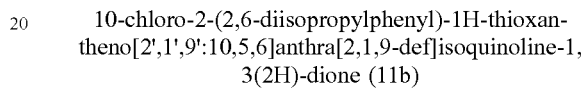

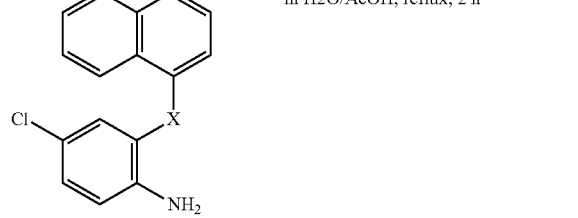

(10b/11b)
10b: X = O
11b: X = S 10-chloro-2-(2,6-diisopropylphenyl)-1H-xantheno[2',1',9':10,5,6]anthra[2,1,9-def]isoquinoline-1,3(2H)-dione (compound 10b)

To compound 17a (0.10 g, 0.160 mmol) in a mixture of acetic acid (6 ml) and concentrated hydrochloric acid (5-6 drops) a solution of sodium nitrite (0.1 g, 1.4 mmol) in water (5 ml) was added dropwise at 0-5° C. under argon steam. The solution of copper(II) sulfate (0.160 g, 1 mmol) in water (6 ml) and acetic acid (2 ml) was poured to the reaction mixture and refluxed for 1.5-2 h to afford the blue solid. The precipitate was filtered, washed with water and water/methanol 1:1. The crude product was dissolved in THF and precipitated in water/methanol 1:2 or purified by column chromatography using toluene as eluent on silica. Yield: 51% (0.05 g, 0.083 mmol).

$^1$H NMR (300 MHz, 298K) δ 1.07 (d, J=6.8 Hz, 12H), 2.63 (h, J=, 6.8 Hz, 2H), 7.25-7.11 (m, 5H) 7.37 (d, J=7.5 Hz, 1H), 7.75 (d, J=8.3 Hz, 1H), 7.81 (d, J=8.6 Hz, 1H), 8.23 (d, J=8.3 Hz, 1H), 8.30 (d, J=8.2 Hz, 1H), 8.41 (t, J=9.2 Hz, 1H), 8.51 (dd, J=8.1, 2.3 Hz, 2H).

FD mass spectrum (8 kV): m/z (%): calcd for 606.11. found: 605.6 (100) [M]$^+$ 10-chloro-2-(2,6-diisopropylphenyl)-1H-thioxantheno[2',1',9':10,5,6]anthra[2,1,9-def]isoquinoline-1,3(2H)-dione (11b)

To compound 17b (0.10 g, 0.156 mmol) in a mixture of acetic acid (6 ml) and concentrated hydrochloric acid (5-6 drops) a solution of sodium nitrite (0.1 g, 1.4 mmol) in water (5 ml) was added dropwise at 0-5° C. under argon steam. The solution of copper(II) sulfate (0.160 g, 1 mmol) in water (6 ml) and acetic acid (2 ml) was poured to the reaction mixture and refluxed for 1,5-2 h to afford the blue solid. The precipitate was filtered, washed with water and water/methanol 1:1. The crude product was dissolved in THF and precipitated in water/methanol 1:2 or purified by column chromatography using toluene as eluent on silica. Yield: 57% (0.055 g, 0.083 mmol)

FD mass spectrum (8 kV): m/z (%): calcd for 622.17. found: 621.50 (100) [M]$^+$

Preparation of Compound 10c and 11c

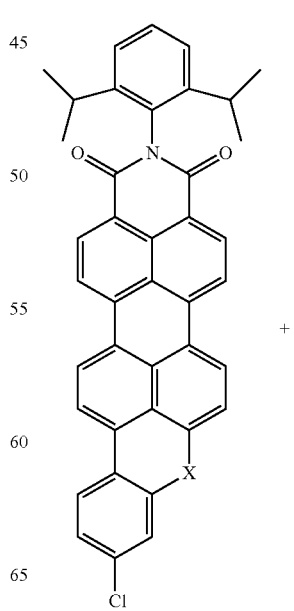

+

-continued

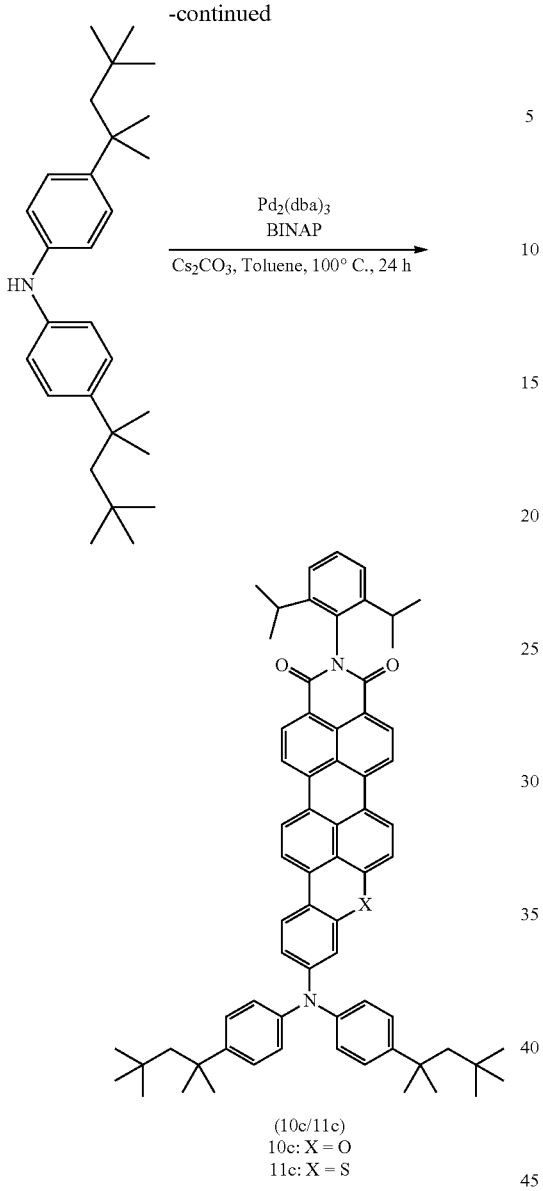

(10c/11c)
10c: X = O
11c: X = S 10-(bis(4-(2,4,4-trimethylpentan-2-yl)phenyl) amino)-2-(2,6-diisopropylphenyl)-1H-xantheno[2',1', 9':10,5,6]anthra[2,1,9-def]isoquinoline-1,3(2H)-dione (10c)

A mixture of compound 18a (0.10 g, 0.165 mmol), bis(4-(2,4,4-trimethylpentan-2-yl)phenyl)amine (0.08 g, 0.2 mmol), Pd$_2$(dba)$_3$ (5 mmol %), BINAP (10 mol %), cesium carbonate (0.1 g, 0.33 mmol) in 20 ml toluene was stirred at 100° C. under argon atmosphere overnight. The solvent was removed under reduced pressure. The crude product was purified by column chromatography using Toluene/EtOAc (4:1) as eluent on silica. Yield: 75% (0.12 g, 0.125 mmol) of a blue solid.

$^1$H NMR (700 MHz, CD$_2$Cl$_2$, 298K) δ 0.81, (s, 18H), 1.15 (dd, J=8.2, 7.0 Hz, 6H), 1.41 (s, 12H), 1.48 (s, 4H), 2.77 (hept, J=6.8 Hz, 2H), 6.54 (d, J=8.2 Hz, 1H), 6.74 (d, J=2.3 Hz, 1H), 6.84 (dd, J=8.5, 2.3 Hz, 1H), 7.16 (d, J=8.6 Hz, 4H), 7.18 (d, J=8.3 Hz, 1H), 7.35 (d, J=8.1 Hz, 2H), 7.39 (d, J=8.6 Hz, 4H), 7.51 (t, J=8.1 Hz, 1H), 7.57 (d, J=9.1 Hz, 1H), 7.60 (d, J=8.2 Hz, 1H), 7.64 (d, J=8.3 Hz, 1H), 7.67 (d, J=4.0 Hz, 1H), 7.69 (d, J=3.6 Hz, 1H), 8.15 (d, J=7.9 Hz, 1H), 8.23 (d, J=7.9 Hz, 1H).

FD mass spectrum (8 kV): m/z (%): calcd for 963.29. found: 963.20 (100) [M]$^+$

UV-Vis (CH$_2$Cl$_2$): $\lambda_{max}$=627 nm (53384 M$^{-1}$ cm$^{-1}$).

10-(bis(4-(2,4,4-trimethylpentan-2-yl)phenyl) amino)-2-(2,6-diisopropylphenyl)-1H-thioxantheno [2',1',9':10,5,6]anthra[2,1,9-def]isoquinoline-1,3 (2H)-dione (11c)

A mixture of compound 18b (0.10 g, 0.160 mmol), bis(4-(2,4,4-trimethylpentan-2-yl)phenyl)amine (0.08 g, 0.2 mmol), Pd$_2$(dba)$_3$ (5 mmol %), BINAP (10 mol %), cesium carbonate (0.1 g, 0.33 mmol) in 20 ml toluene was stirred at 100° C. under argon atmosphere overnight. The solvent was removed under reduced pressure. The crude product was purified by column chromatography using Toluene/EtOAc (4:1) as eluent on silica. Yield: 73% (0.115 g, 0.117 mmol) of a blue solid.

$^1$H NMR (300 MHz, CD$_2$Cl$_2$, 298K) 0.71 (s, 18H), 1.07 (dd, J=6.8, 2.3 Hz, 6H), 1.32 (d, J=2.8 Hz, 12H), 1.64 (s, 4H), 2.69 (h, J=6.7 Hz, 2H), 6.70 (d, J=2.5 Hz, 1H), 6.78-6.90 (m, 2H), 7.05 (m, 4H), 7.17-7.36 (m, 5H), 7.36-7.52 (m, 2H), 7.64 (d, J=8.2 Hz, 1H), 7.69 (d, J=5.5 Hz, 1H), 7.71-7.79 (m, 2H), 8.18 (d, J=8.1 Hz, 2H), 8.23 (d, J=8.2 Hz, 2H).

FD mass spectrum (8 kV): m/z (%): calcd for 976.36. found: 979.30 (100) [M]$^+$

UV-Vis (CH$_2$Cl$_2$): $\lambda_{max}$=659 nm (54533 M$^{-1}$cm$^{-1}$).

Preparation of Compound 10

10-(bis(4-(2,4,4-trimethylpentan-2-yl)phenyl)amino) isochromeno[6',5',4':10,5,6]anthra[2,1,9-mna]xanthene-1,3-dione

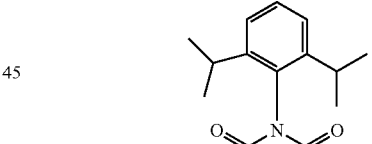

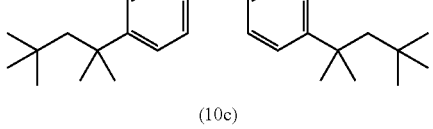

(10c)

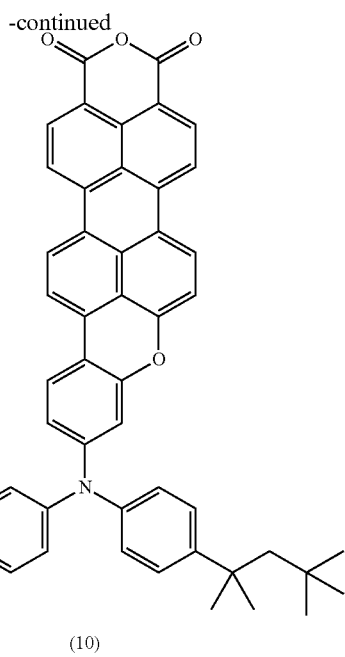

(10)

A mixture of potassium hydroxide (0.5 g) and Compound 10c (0.10 g, 0.104 mmol) in 10 ml 2-Methyl-2-butanol was stirred and reflused overnight. The mixture was cooled and diluted with 50 ml 10% hydrochloric acid. The precipitate was filtered, washed with water and dried. The solid was suspended in the mixture of DCM (10 ml) and acetic acid (20 ml) with 4-5 drops of acetic anhydride and stirred overnight at 100° C. The mixture was cooling down to room temperature and 10 ml of water was added. The precipitate was filtered, washed with water/methanol 1:2 and dried. The product was obtained and isolated as blue solid in 96% yield (0.08 g, 0.1 mmol).

FD mass spectrum (8 kV): m/z (%): calcd for 804.02. found: 804.10 (100) [M]$^+$.

Preparation of Compound 12

2-(10-(bis(4-(2,4,4-trimethylpentan-2-yl)phenyl)amino)-1,3-dioxo-1H-xantheno[2',1',9':10,5,6]anthra[2,1,9-def]isoquinolin-2(3H)-yl)acetic acid

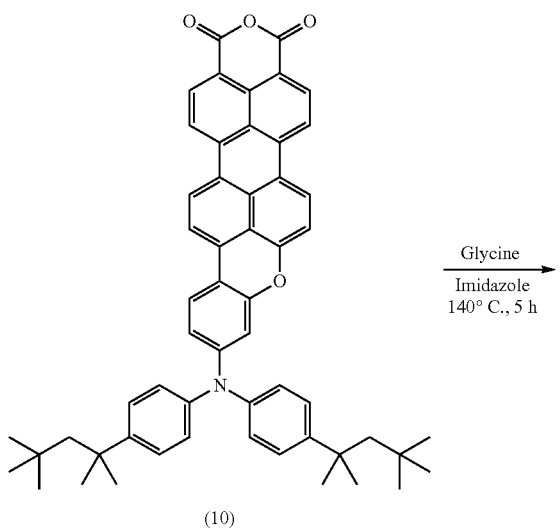

(10)

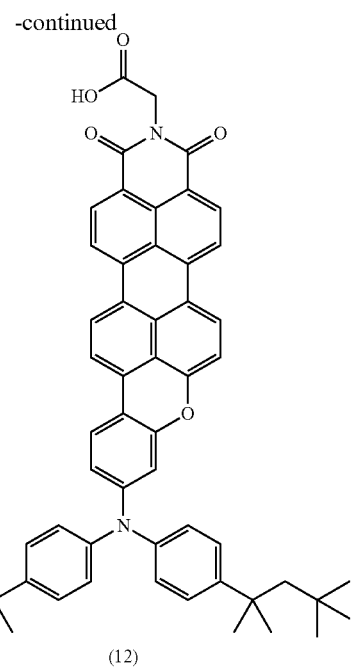

(12)

A mixture of Compound 10 (0.06 g, 0.08 mmol), glycine (1.0 g) and imidazole (3.0 g) was stirred at 140° C. under argon atmosphere for 4 h. The mixture was poured into 10% hydrochloric acid and ice. The precipitate was filtered, washed with water and water/methanol 1:1. The crude product was dissolved in THF and precipitated in water/methanol 1:2. The solid was dissolved in THF and purified by GPC using THF as eluent. The product was obtained and isolated as blue solid in 58% yield (0.04 g, 0.047 mmol).

FD mass spectrum (8 kV): m/z (%): calcd for 861.08. found: 861.7 (100) [M]$^+$

UV-Vis (CH$_2$Cl$_2$): $\lambda_{max}$=609 nm (54533 M$^{-1}$cm$^{-1}$).

B) Preparation and Characterization of the DSCs

General Methods and Materials

Preparation of the (solid-state) DSCs: A TiO$_2$ blocking layer was prepared on a fluorine-doped tin oxide (FTO)-covered glass substrate using spray pyrolysis (cf. B. Peng, G. Jungmann, C. Jager, D. Haarer, H. W. Schmidt, M. Thelakkat, Coord. Chem. Rev. 2004, 248, 1479). Next, a TiO$_2$ paste (Dyesol), diluted with terpineol, was applied by screen printing, resulting in a film thickness of 1.7 µm. All films were then sintered for 45 min at 450° C., followed by treatment in a 40 mM aqueous solution of TiCl$_4$ at 60° C. for 30 min, followed by another sintering step. The prepared samples with TiO$_2$ layers were pretreated with 5 mM solutions of either the additive 2-(p-butoxyphenyl)aceto-hydroxamic acid sodium salt ("ADD1") or the additive 2-(p-butoxyphenyl)aceto-hydroxamic acid tetrabutyl ammonium salt ("ADD2") in ethanol. These additives are described on page 52 and page 53 of WO 2012/001628 A1 as "Example No. 6" and "Example No. 10", respectively. The electrodes were then dyed in 0.5 mM dye solution in toluene or CH$_2$Cl$_2$ (DCM) (solvent listed in table 1). Spiro-MeOTAD was applied by spin-coating from a solution in DCM (200 mg/mL) also containing 20 mM Li(CF$_3$SO$_2$)$_2$N. Fabrication of the device was completed by evaporation of 200 nm of silver as the counter electrode. The active area of the sDSC was defined by the size of these contacts (0.13 cm$^2$), and the cells were masked by an aperture of the same area for measurements. The current-voltage characteristics for all cells were measured with a Keithley 2400 under 1000 W/m², AM 1.5G conditions (LOT ORIEL 450 W). The incident photon to current conversion efficiency's (IPCE) were obtained with an Acton Research Monochromator using additional white background light illumination.

The samples were illuminated with monochromatic light from the quartz monochromator with deuterium lamp. The power of the incident light beam was $(2-5) \cdot 10^{-8}$ W. The negative voltage of −300 V was supplied to the sample substrate. The counter-electrode with the 4.5×15 mm² slit for illumination was placed at 8 mm distance from the sample surface. The counter-electrode was connected to the input of the BK2-16 type electrometer, working in the open input regime, for the photocurrent measurement. The $10^{-15}$-$10^{-12}$ A strong photocurrent was flowing in the circuit under illumination. The photocurrent J is strongly dependent on the incident light photon energy hv. The $J^{0.5}=f(h\nu)$ dependence was plotted. Usually the dependence of the photocurrent on incident light quanta energy is well described by linear relationship between $J^{0.5}$ and hv near the threshold (cf. E. Miyamoto, Y. Yamaguchi, M. Yokoyama, Electrophotography 1989, 28, 364 and M. Cordona, L. Ley, Top. Appl. Phys. 1978, 26, 1). The linear part of this dependence was extrapolated to the hv axis and $J_p$ value was determined as the photon energy at the interception point.

The results of the DSCs with varying dyes/compounds are given in the following table 1.

TABLE 1

| | Isc [mA/cm²] | Voc [mV] | FF [%] | ETA [%] | Sun [mW/cm²] |
|---|---|---|---|---|---|
| ADD1 before, compound 8, toluene | −6.25 | 700 | 62 | 2.7 | 100 |
| ADD2 before, compound 8, toluene | −5.79 | 720 | 65 | 2.7 | 100 |
| ADD1 before, compound 12, DCM | −3.38 | 640 | 58 | 1.3 | 100 |
| ADD2 before, compound 12, DCM | −2.84 | 660 | 61 | 1.1 | 100 |
| ADD1 before, compound 2, DCM | −2.16 | 740 | 67 | 1.1 | 100 |
| ADD2 before, compound 2, DCM | −2.91 | 740 | 62 | 1.3 | 100 |
| ADD1 before, compound 5, DCM | −1.36 | 580 | 59 | 0.5 | 100 |
| ADD2 before, compound 5, DCM | −1.47 | 560 | 62 | 0.5 | 100 |

Isc: short circuit current;
Voc: open circuit voltage;
FF: fill factor;
ETA: efficiency

Figure 1:
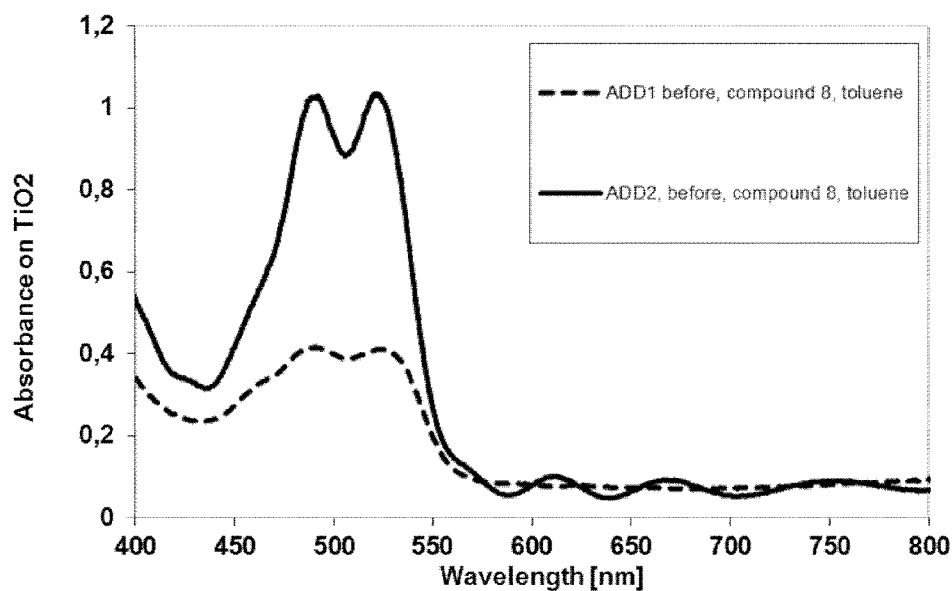
FIG. 1: Absorbance of compound 8 on $TiO_2$ with additives ADD1 and ADD2 before coating with the hole conductor
Figure 2:
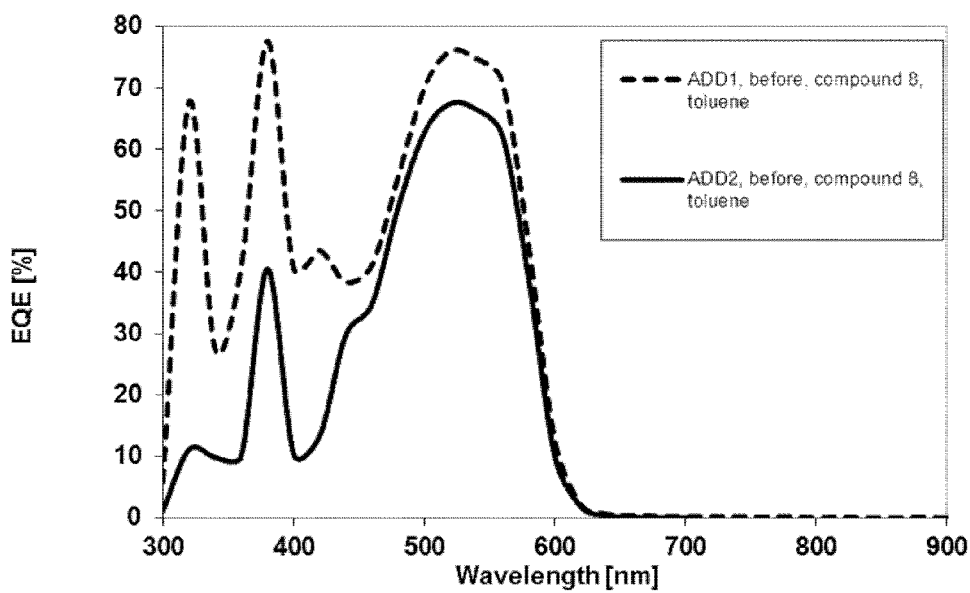
FIG. 2: EQE of the OPV cell in the case of use of compound 8 (applied as toluene solution) with ADD1 and ADD2 before coating with the hole conductor
Figure 3:
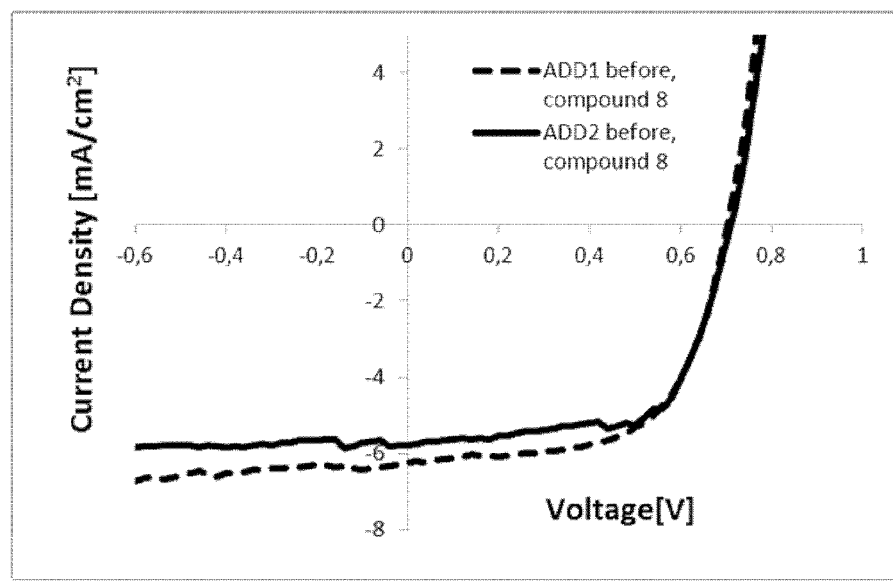
FIG. 3: Current-voltage characteristic of the OPV cell in the case of use of compound 8 with additives ADD1 and ADD2 before coating with the hole conductor
Figure 4:
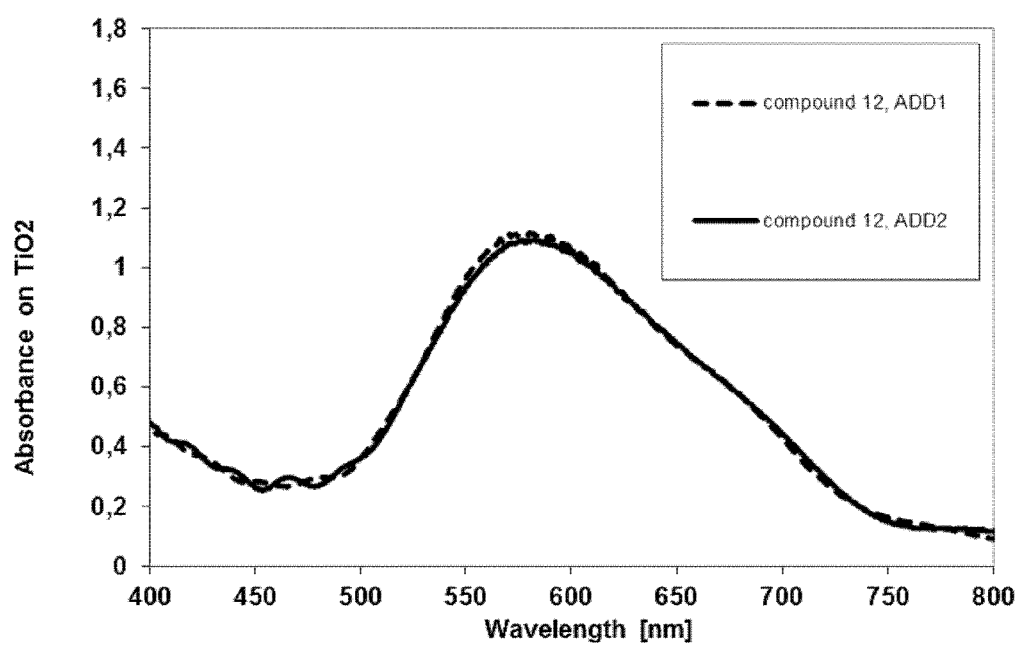
FIG. 4: Absorbance of compound 12 on $TiO_2$ with additives ADD1 and ADD2 before coating with the hole conductor
Figure 5:
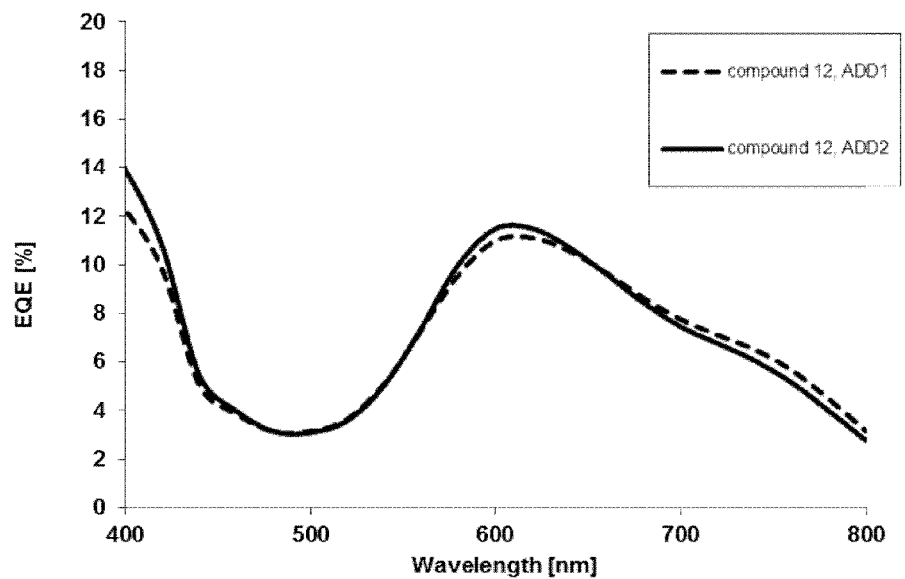
FIG. 5: EQE of the OPV cell in the case of use of compound 12 (applied as DCM solution) with ADD1 and ADD2 before coating with the hole conductor
Figure 6:
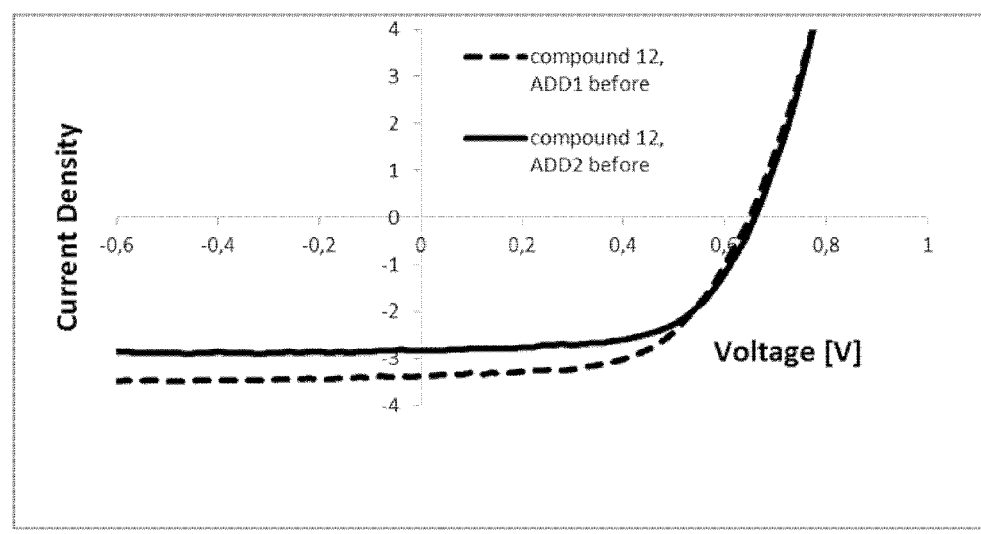
FIG. 6: Current-voltage characteristic of the OPV cell in the case of use of compound 12 with additives ADD1 and ADD2 before coating with the hole conductor
Figure 7:
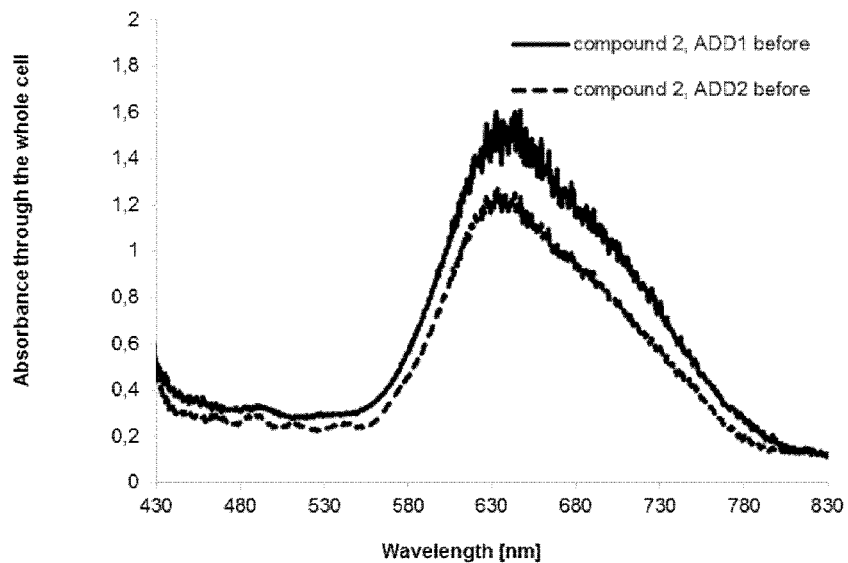
FIG. 7: Absorbance of compound 2 on $TiO_2$ with additives ADD1 and ADD2 before coating with the hole conductor
Figure 8:
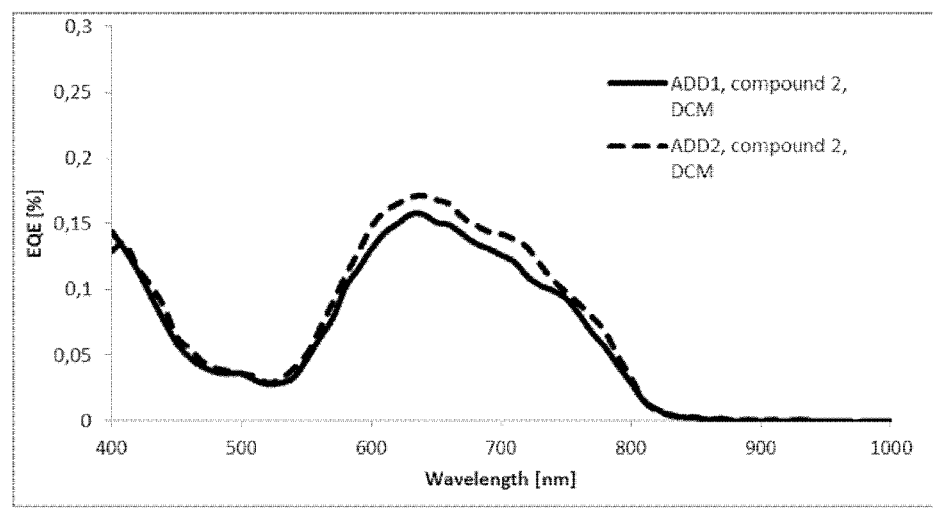
FIG. 8: EQE of the OPV cell in the case of use of compound 2 (applied as DCM solution) with ADD1 and ADD2 before coating with the hole conductor
Figure 9:
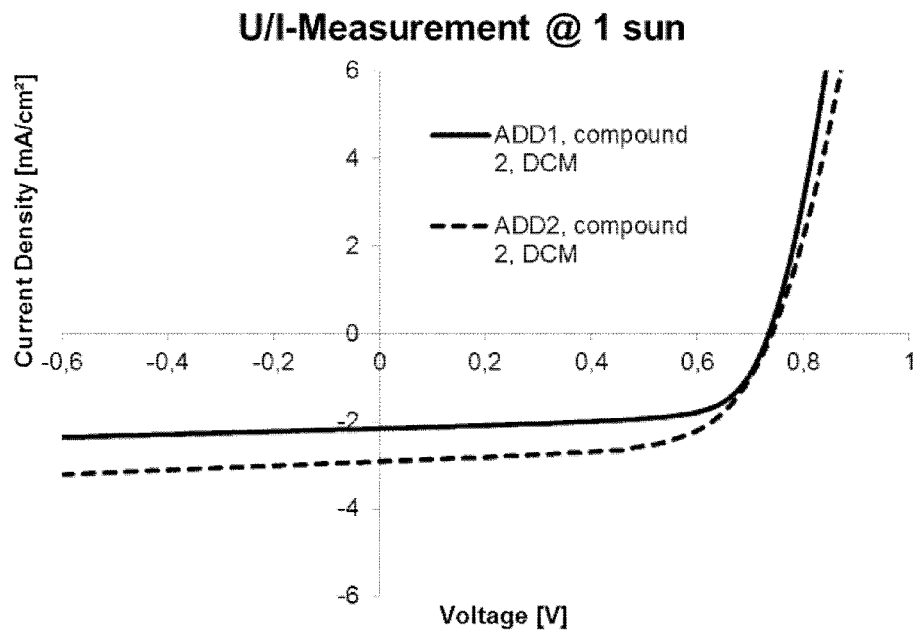
FIG. 9: Current-voltage characteristic of the OPV cell in the case of use of compound 2 with additives ADD1 and ADD2 before coating with the hole conductor
Figure 10:
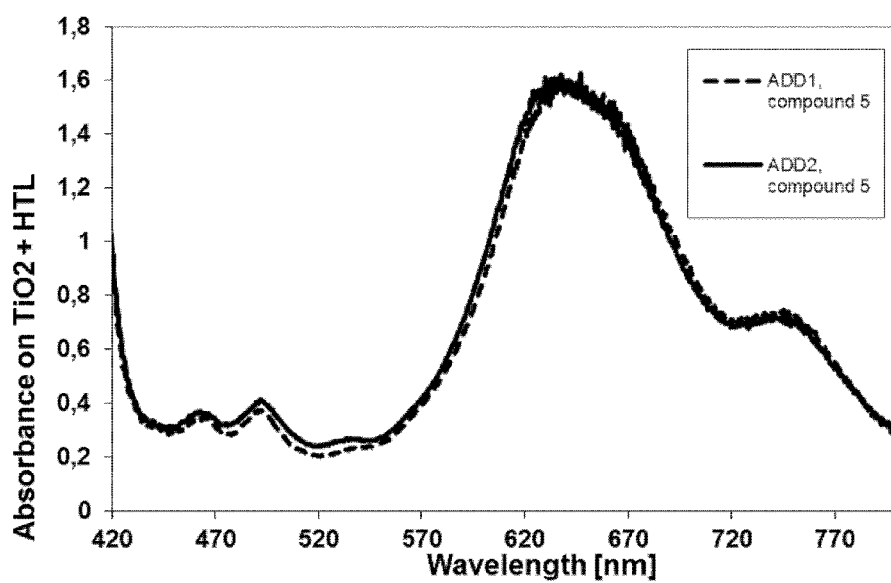
FIG. 10: Absorbance of compound 5 on $TiO_2$ with additives ADD1 and ADD2 before coating with the hole conductor
Figure 11:
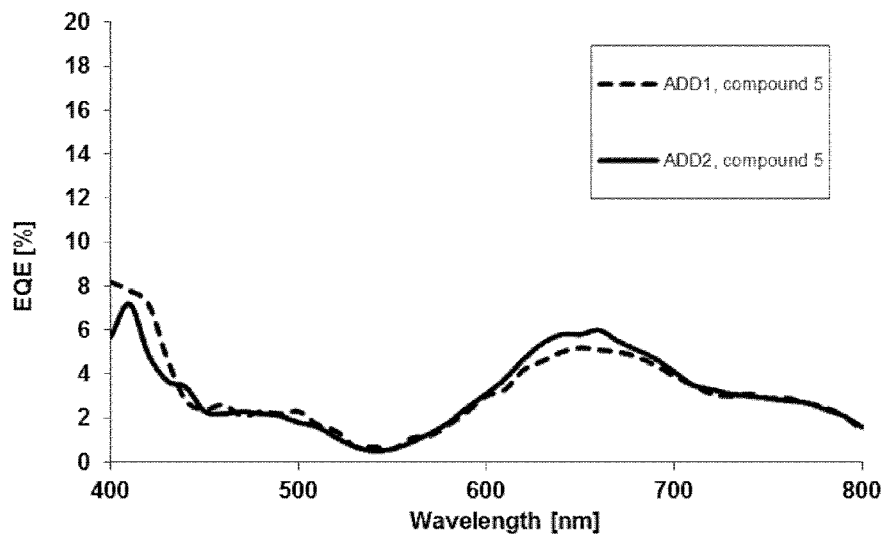
FIG. 11: EQE of the OPV cell in the case of use of compound 5 (applied as DCM solution) with ADD1 and ADD2 before coating with the hole conductor
Figure 12:
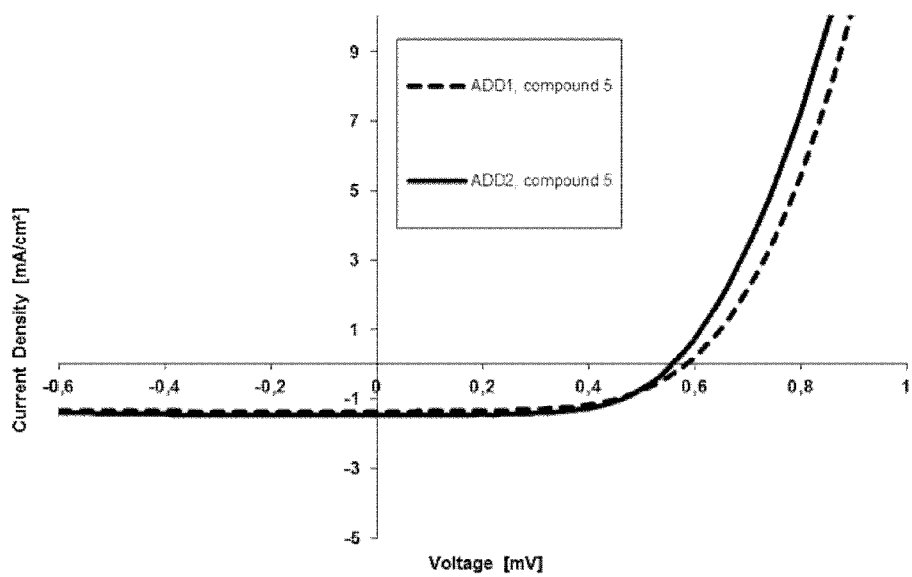
FIG. 12: Current-voltage characteristic of the OPV cell in the case of use of compound 5 with additives ADD1 and ADD2 before coating with the hole conductor

The invention claimed is:
1. A sensitizer in a dye-sensitized solar cell, comprising a compound of formula (I'):

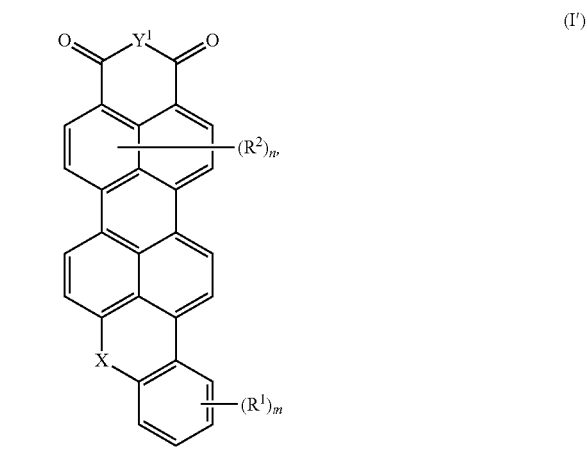

(I')

wherein:
R¹, R² are each independently hydrogen, a halogen, an alkyl group, a cycloalkyl group, an aryl group, a hetaryl group, an alkoxy group, an aryloxy group, an arylthio group, a hetaryloxy group, a hetarylthio group, a diarylamino group, or a dialkylamino group;
m, n are each independently an integer of 0, 1, 2, 3, or 4;
X is sulfur, oxygen, or NR³, where R³ is hydrogen, an alkyl group, a cycloalkyl group, an aryl group, or a hetaryl group; and $Y^1$ is oxygen or N—Z-A, wherein:

A is —COOM, —$SO_3M$, or —$PO_3M$, where M is hydrogen, an alkali metal cation, or $[NR']^{4+}$, where each R' is independently hydrogen or an alkyl group; and Z is $C_1$-$C_6$-alkylene or 1,4-phenylene, where the phenylene radical is optionally substituted by one or more alkyl, nitro, cyano and/or halogen substituents.

2. The sensitizer according to claim 1, wherein, in formula (I'):

$R^1$, $R^2$ are each independently hydrogen, a halogen atom, an aryl group, an aryloxy group, an arylthio group, a hetaryloxy group, a hetarylthio group, or a dialkylamino group;

m, n are each independently an integer of 0, 1, or 2;

$R^3$ is an alkyl or aryl group;

A is —COOM; and

Z is $C_1$-$C_6$-alkylene or 1,4-phenylene.

3. A method for making a compound of formula (I'):

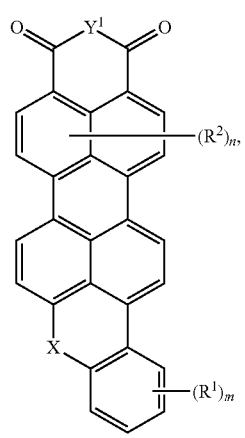

(I')

wherein:

$R^1$, $R^2$ are each independently hydrogen, a halogen, an alkyl group, a cycloalkyl group, an aryl group, a hetaryl group, an alkoxy group, an aryloxy group, an arylthio group, a hetaryloxy group, a hetarylthio group, a diarylamino group, or a dialkylamino group;

m, n are each independently an integer of 0, 1, 2, 3, or 4;

X is sulfur, oxygen, or $NR^3$, where $R^3$ is hydrogen, an alkyl group, a cycloalkyl group, an aryl group, or a hetaryl group; and $Y^1$ is oxygen or N—Z-A, wherein:

A is —COOM, —$SO_3M$, or —$PO_3M$, where M is hydrogen, an alkali metal cation, or $[NR']^{4+}$, where each R' is independently hydrogen or an alkyl group; and Z is $C_1$-$C_6$-alkylene or 1,4-phenylene, where the phenylene radical is optionally substituted by one or more alkyl, nitro, cyano and/or halogen substituents, the method comprising:

reacting a compound of formula (II) with a hydroxide alkaline agent or reacting the compound of formula (II) with a hydroxide alkaline agent and then an amine of formula (III):

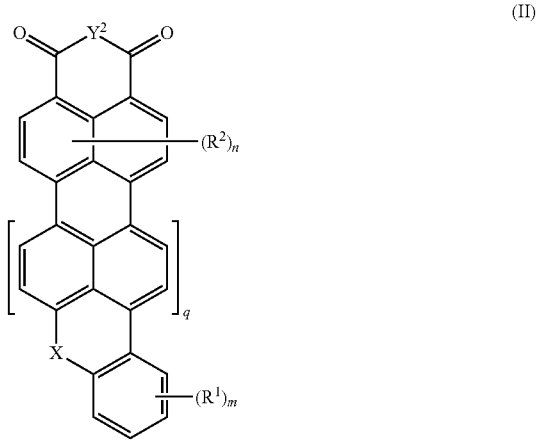

(II)

wherein:

$R^1$, $R^2$ are each independently hydrogen, a halogen atom, an alkyl group, a cycloalkyl group, an aryl group, a hetaryl group, an alkoxy group, an aryloxy group, an arylthio group, a hetaryloxy group, a hetarylthio group, a diarylamino group, or a dialkylamino group;

m, n are each independently an integer of 0, 1, 2, 3, or 4;

q is 1;

X is sulfur, oxygen, or $NR^3$, where $R^3$ is hydrogen, an alkyl group, a cycloalkyl group, an aryl group, or a hetaryl group, and $Y^2$ is $NR^4$, where $R^4$ is hydrogen, an alkyl group, a cycloalkyl group, an aryl group or a hetaryl group, $H_2N$—Z-A (III)

wherein:

A is —COOM, —$SO_3M$, or —$PO_3M$, where M is hydrogen, an alkali metal cation, or $[NR']^{4+}$, where each R' is independently hydrogen or an alkyl group: and Z is $C_1$-$C_6$-alkylene or 1,4-phenylene, where the phenylene radical is optionally substituted by one or more alkyl, nitro, cyano and/or halogen substituents.

4. The method according to claim 3, wherein, in formula (II):

$R^1$, $R^2$ are each independently hydrogen, a halogen atom, an aryl group, an aryloxy group, an arylthio group, a hetaryloxy group, a hetarylthio group, or a dialkylamino group;

m, n are each independently an integer of 0, 1, or 2; and

X is sulfur, oxygen, or $NR^3$, where $R^3$ is an alkyl or aryl group.

5. A dye-sensitized solar cell, comprising:
a compound of formula (I')

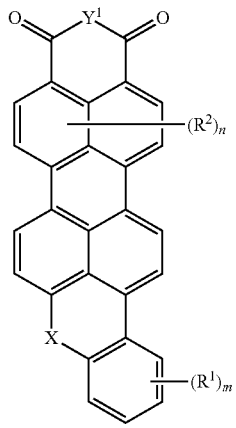

wherein:
R$^1$, R$^2$ are each independently hydrogen, a halogen, an alkyl group, a cycloalkyl group, an aryl group, a hetaryl group, an alkoxy group, an aryloxy group, an arylthio group, a hetaryloxy group, a hetarylthio group, a diarylamino group, or a dialkylamino group;

m, n are each independently an integer of 0, 1, 2, 3, or 4;

X is sulfur, oxygen, or NR$^3$, where R$^3$ is hydrogen, an alkyl group, a cycloalkyl group, an aryl group, or a hetaryl group; and Y$^1$ is oxygen or N—Z-A, wherein:
A is —COOM, —SO$_3$M, or —PO$_3$M, where M is hydrogen, an alkali metal cation, or [NR']$^{4+}$, where each R' is independently hydrogen or an alkyl group; and Z is C$_1$-C$_6$-alkylene or 1,4-phenylene, where the phenylene radical is optionally substituted by one or more alkyl, nitro, cyano and/or halogen substituents.

6. The dye-sensitized solar cell according to claim 5, wherein, in formula (I'):
R$^1$, R$^2$ are each independently hydrogen, a halogen atom, an aryl group, an aryloxy group, an arylthio group, a hetaryloxy group, a hetarylthio group, or a dialkylamino group;

m, n are each independently an integer of 0, 1, or 2;

R$^3$ is an alkyl or aryl group;

A is —COOM; and

Z is C$_1$-C$_6$-alkylene or 1,4-phenylene.

* * * * *